US012773341B2

(12) United States Patent
Johannes et al.

(10) Patent No.: US 12,773,341 B2
(45) Date of Patent: Oct. 27, 2026

(54) FLUID COLLECTION DEVICES, SYSTEMS AND METHODS

(71) Applicant: PureWick Corporation, El Cajon, CA (US)

(72) Inventors: Ashley Marie Johannes, Atlanta, GA (US); Pranav Challa, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 1224 days.

(21) Appl. No.: 17/625,887

(22) PCT Filed: Jul. 8, 2020

(86) PCT No.: PCT/US2020/041242
§ 371 (c)(1),
(2) Date: Jan. 10, 2022

(87) PCT Pub. No.: WO2021/007345
PCT Pub. Date: Jan. 14, 2021

(65) Prior Publication Data

US 2022/0257407 A1 Aug. 18, 2022

Related U.S. Application Data

(60) Provisional application No. 62/873,045, filed on Jul. 11, 2019.

(51) Int. Cl.
*A61F 5/453* (2006.01)
*A61F 5/455* (2006.01)

(52) U.S. Cl.
CPC .............. *A61F 5/453* (2013.01); *A61F 5/455* (2013.01)

(58) Field of Classification Search
CPC ................................ A61F 5/455; A61F 5/453
See application file for complete search history.

(56) References Cited

U.S. PATENT DOCUMENTS

| | | | |
|---|---|---|---|
| 737,443 | A | 8/1903 | Mooers |
| 976,883 | A | 11/1910 | Keagy et al. |
| 1,015,905 | A | 1/1912 | Northrop |
| 1,032,841 | A | 7/1912 | Koenig |
| 1,178,644 | A | 4/1916 | Johnson |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Rebecca E Eisenberg
*Assistant Examiner* — Gabriella E Burnette
(74) *Attorney, Agent, or Firm* — Ballard Spahr LLP

(57) ABSTRACT

Examples relate to devices, systems, and methods for fluid collection such as urine. The fluid collection device is shaped to complement the female anatomy or male anatomy near the urethra. The fluid impermeable coating of the fluid collection device is sized and shaped to provide a soft, smooth, and compliant outer surface for the fluid collection device. The fluid collection device may be coupled to a vacuum source via one or more sections of conduit.

20 Claims, 11 Drawing Sheets

(56) References Cited

U.S. PATENT DOCUMENTS

| | | | |
|---|---|---|---|
| 1,229,423 A | | 6/1917 | Eckenrode |
| 1,387,726 A | | 8/1921 | Karge |
| 1,742,080 A | | 12/1929 | Jones |
| 1,979,899 A | | 11/1934 | Obrien et al. |
| 2,241,010 A | | 5/1941 | Chipley |
| 2,262,772 A | | 11/1941 | Peder |
| 2,326,881 A | | 8/1943 | Packer |
| 2,379,346 A | | 6/1945 | Farrell |
| 2,485,555 A | | 10/1949 | Bester |
| 2,571,357 A | | 10/1951 | Charles |
| 2,613,670 A | | 10/1952 | Edward |
| 2,616,426 A | | 11/1952 | Adele |
| 2,644,234 A | | 7/1953 | Earl |
| 2,648,335 A | | 8/1953 | Chambers |
| 2,789,560 A | | 4/1957 | Weimer |
| 2,859,786 A | | 11/1958 | Tupper |
| 2,944,551 A | | 7/1960 | Carl |
| 2,968,046 A | | 1/1961 | Duke |
| 2,971,512 A | | 2/1961 | Reinhardt |
| 3,032,038 A | | 5/1962 | Swinn |
| 3,077,883 A | | 2/1963 | Hill |
| 3,087,938 A | | 4/1963 | Hans et al. |
| 3,114,916 A | | 12/1963 | Hadley |
| 3,169,528 A | | 2/1965 | Knox et al. |
| 3,171,506 A | | 3/1965 | Therkel |
| 3,175,719 A | | 3/1965 | Herndon |
| 3,194,238 A | | 7/1965 | Breece |
| 3,198,994 A | | 8/1965 | Hildebrandt et al. |
| 3,221,742 A | | 12/1965 | Egon |
| 3,312,221 A | | 4/1967 | Overment |
| 3,312,981 A | | 4/1967 | Mcguire et al. |
| 3,340,876 A | | 9/1967 | Hill |
| 3,349,768 A | | 10/1967 | Keane |
| 3,356,091 A | | 12/1967 | Patterson |
| 3,362,590 A | | 1/1968 | Gene |
| 3,366,116 A | | 1/1968 | Huck |
| 3,368,564 A | | 2/1968 | Selix |
| 3,369,940 A | | 2/1968 | Slautterback |
| 3,398,848 A | | 8/1968 | Donovan |
| 3,400,717 A | | 9/1968 | Bruce et al. |
| 3,406,688 A | | 10/1968 | Bruce |
| 3,411,504 A | * | 11/1968 | Glassman ......... A61F 13/47218 604/380 |
| 3,424,163 A | | 1/1969 | Gravdahl |
| 3,425,471 A | | 2/1969 | Yates |
| 3,434,565 A | | 3/1969 | Fischer |
| 3,447,536 A | | 6/1969 | Snyder |
| 3,511,241 A | | 5/1970 | Lee |
| 3,512,185 A | | 5/1970 | Ellis |
| 3,520,300 A | | 7/1970 | Flower |
| 3,528,423 A | | 9/1970 | Lee |
| 3,608,552 A | | 9/1971 | Broerman |
| 3,613,123 A | | 10/1971 | Langstrom |
| 3,648,700 A | | 3/1972 | Warner |
| 3,651,810 A | | 3/1972 | Ormerod |
| 3,661,155 A | | 5/1972 | Lindan |
| 3,683,918 A | | 8/1972 | Pizzella |
| 3,690,315 A | | 9/1972 | Chittenden et al. |
| 3,699,815 A | | 10/1972 | Holbrook |
| 3,720,554 A | | 3/1973 | Stumpf |
| 3,721,243 A | | 3/1973 | Greth et al. |
| 3,726,277 A | | 4/1973 | Hirschman |
| 3,727,788 A | | 4/1973 | Holbrook |
| 3,730,411 A | | 5/1973 | Brockmuller |
| 3,742,952 A | | 7/1973 | Magers et al. |
| 3,742,953 A | | 7/1973 | Lee |
| 3,757,355 A | | 9/1973 | Allen et al. |
| 3,788,324 A | | 1/1974 | Lim |
| 3,843,016 A | | 10/1974 | Bornhorst et al. |
| 3,863,638 A | | 2/1975 | Rogers et al. |
| 3,863,798 A | | 2/1975 | Kurihara et al. |
| 3,864,759 A | | 2/1975 | Horiuchi |
| 3,865,109 A | | 2/1975 | Elmore et al. |
| 3,881,486 A | | 5/1975 | Fenton |
| 3,881,489 A | | 5/1975 | Hartwell |
| 3,887,032 A | | 6/1975 | Harris |
| 3,915,189 A | | 10/1975 | Holbrook et al. |
| 3,931,650 A | | 1/1976 | Miller |
| 3,931,819 A | | 1/1976 | Weedle |
| 3,964,786 A | | 6/1976 | Mashuda |
| 3,998,228 A | | 12/1976 | Poidomani |
| 3,999,550 A | | 12/1976 | Martin |
| 4,006,793 A | | 2/1977 | Robinson |
| 4,015,604 A | | 4/1977 | Csillag |
| 4,020,843 A | | 5/1977 | Kanall |
| 4,022,211 A | | 5/1977 | Timmons et al. |
| 4,022,213 A | | 5/1977 | Stein |
| 4,023,216 A | | 5/1977 | Li |
| 4,027,776 A | | 6/1977 | Douglas |
| 4,031,897 A | | 6/1977 | Graetz |
| 4,042,337 A | | 8/1977 | Griffith |
| 4,064,962 A | | 12/1977 | Hunt |
| 4,069,817 A | | 1/1978 | Fenole et al. |
| 4,084,589 A | | 4/1978 | Kulvi |
| 4,096,897 A | | 6/1978 | Cammarata |
| 4,116,197 A | | 9/1978 | Bermingham |
| 4,140,739 A | | 2/1979 | Cotten |
| 4,180,178 A | | 12/1979 | Turner |
| 4,187,953 A | | 2/1980 | Turner |
| 4,194,508 A | | 3/1980 | Anderson |
| 4,197,849 A | | 4/1980 | Bostick |
| 4,200,102 A | | 4/1980 | Duhamel et al. |
| 4,202,058 A | | 5/1980 | Anderson |
| 4,203,502 A | | 5/1980 | Strader |
| 4,203,503 A | | 5/1980 | Bertotti et al. |
| 4,209,076 A | | 6/1980 | Bertotti et al. |
| D255,935 S | | 7/1980 | Cullis et al. |
| 4,223,677 A | | 9/1980 | Anderson |
| 4,233,025 A | | 11/1980 | Larson et al. |
| 4,233,978 A | | 11/1980 | Hickey |
| 4,246,901 A | | 1/1981 | Frosch et al. |
| 4,253,542 A | | 3/1981 | Ruspa et al. |
| 4,257,418 A | | 3/1981 | Hessner |
| 4,270,539 A | | 6/1981 | Frosch et al. |
| 4,280,498 A | | 7/1981 | Jensen |
| 4,281,655 A | | 8/1981 | Terauchi |
| 4,292,916 A | | 10/1981 | Bradley et al. |
| 4,330,239 A | | 5/1982 | Gannaway |
| 4,345,341 A | | 8/1982 | Saito |
| 4,349,029 A | | 9/1982 | Mott |
| 4,352,356 A | | 10/1982 | Tong |
| 4,356,012 A | | 10/1982 | Hofstetter |
| 4,360,933 A | | 11/1982 | Kimura et al. |
| 4,365,363 A | | 12/1982 | Windauer |
| 4,372,299 A | | 2/1983 | Fixel |
| 4,375,841 A | | 3/1983 | Vielbig |
| 4,387,726 A | | 6/1983 | Denard |
| 4,403,991 A | | 9/1983 | Hill |
| 4,421,511 A | | 12/1983 | Steer et al. |
| 4,425,130 A | | 1/1984 | Desmarais |
| 4,446,986 A | | 5/1984 | Bowen et al. |
| 4,453,938 A | | 6/1984 | Brendling |
| 4,457,314 A | | 7/1984 | Knowles |
| 4,457,758 A | | 7/1984 | Norton |
| 4,476,879 A | | 10/1984 | Jackson |
| 4,512,771 A | | 4/1985 | Norton |
| 4,526,688 A | | 7/1985 | Schmidt et al. |
| 4,528,703 A | | 7/1985 | Kraus |
| 4,533,354 A | | 8/1985 | Jensen et al. |
| 4,533,357 A | | 8/1985 | Hall |
| D280,438 S | | 9/1985 | Wendt |
| 4,551,141 A | | 11/1985 | Mcneil |
| 4,553,968 A | | 11/1985 | Komis |
| 4,568,341 A | | 2/1986 | Mitchell et al. |
| 4,581,026 A | | 4/1986 | Schneider |
| 4,583,983 A | | 4/1986 | Einhorn et al. |
| 4,589,516 A | | 5/1986 | Inoue et al. |
| 4,601,716 A | | 7/1986 | Smith |
| 4,610,675 A | | 9/1986 | Triunfol |
| 4,620,333 A | | 11/1986 | Ritter |
| 4,626,250 A | | 12/1986 | Schneider |
| 4,627,846 A | | 12/1986 | Ternstroem |
| 4,631,061 A | | 12/1986 | Martin |
| 4,645,275 A | | 2/1987 | Pucci |

(56) References Cited

U.S. PATENT DOCUMENTS 4,650,477 A 3/1987 Johnson
4,655,754 A 4/1987 Richmond et al.
4,656,675 A 4/1987 Fajnsztajn
4,681,570 A 7/1987 Dalton
4,681,572 A 7/1987 Tokarz et al.
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.
4,735,841 A 4/1988 Sourdet
4,743,236 A 5/1988 Manschot
4,747,166 A 5/1988 Kuntz
4,752,944 A 6/1988 Conrads et al.
4,759,753 A 7/1988 Schneider et al.
4,769,215 A 9/1988 Ehrenkranz
4,771,484 A 9/1988 Mozell
4,772,280 A 9/1988 Rooyakkers
4,784,654 A 11/1988 Beecher
4,790,830 A 12/1988 Hamacher
4,790,835 A 12/1988 Elias
4,791,686 A 12/1988 Taniguchi et al.
4,795,449 A 1/1989 Schneider et al.
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,291 A 4/1989 Terauchi et al.
4,820,297 A 4/1989 Kaufman et al.
4,841,728 A 6/1989 Jean et al.
4,846,818 A 7/1989 Keldahl et al.
4,846,819 A 7/1989 Welch
4,846,824 A 7/1989 Lassen et al.
4,846,909 A 7/1989 Klug et al.
4,857,064 A 8/1989 Mendoza
4,865,595 A 9/1989 Heyden
4,872,299 A 10/1989 Troutner et al.
4,875,898 A 10/1989 Eakin
4,880,417 A 11/1989 Yabrov et al.
4,882,794 A 11/1989 Stewart
4,883,465 A 11/1989 Brennan
4,886,498 A 12/1989 Newton
4,886,508 A * 12/1989 Washington ............ A61F 5/455
604/347
4,886,509 A 12/1989 Mattsson
4,889,532 A 12/1989 Metz et al.
4,889,533 A 12/1989 Beecher
4,890,691 A 1/1990 Ching-Ho
4,895,140 A 1/1990 Bellak
4,903,254 A 2/1990 Haas
4,904,248 A 2/1990 Vaillancourt
D306,759 S 3/1990 D'Alo
4,905,692 A 3/1990 More
4,911,262 A 3/1990 Tani et al.
4,930,997 A 6/1990 Bennett
4,936,838 A 6/1990 Cross et al.
4,950,262 A 8/1990 Takagi
4,955,922 A 9/1990 Terauchi
4,957,487 A 9/1990 Gerow
4,963,134 A 10/1990 Backscheider et al.
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,013,308 A 5/1991 Sullivan et al.
5,030,229 A 7/1991 Yang
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 McGuire
5,078,707 A 1/1992 Peter
5,084,037 A 1/1992 Barnett
5,100,396 A 3/1992 Zamierowski
5,102,404 A 4/1992 Goldberg et al.
5,112,324 A 5/1992 Wallace
5,134,994 A 8/1992 Say
5,137,033 A 8/1992 Norton
5,147,301 A 9/1992 Ruvio
5,176,667 A 1/1993 Debring
5,195,997 A 3/1993 Carns
5,196,654 A 3/1993 Diflora et al.
5,199,444 A 4/1993 Wheeler
5,203,699 A 4/1993 McGuire
5,220,137 A 6/1993 Howerton et al.
5,234,419 A 8/1993 Bryant et al.
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,979 A 3/1994 Delaurentis et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,457 A 7/1994 Cohen
5,330,459 A 7/1994 Lavon et al.
5,334,174 A 8/1994 Street
5,334,176 A 8/1994 Buenger et al.
5,340,840 A 8/1994 Park et al.
D354,129 S 1/1995 Salvadori
D354,560 S 1/1995 Chase
5,382,244 A 1/1995 Telang
5,397,315 A 3/1995 Schmidt et al.
5,409,014 A 4/1995 Napoli et al.
5,409,475 A 4/1995 Steer
5,411,495 A 5/1995 Willingham
5,423,784 A 6/1995 Metz
5,423,788 A 6/1995 Rollins et al.
5,437,836 A 8/1995 Yamada
5,455,091 A 10/1995 Oreglia et al.
5,456,246 A 10/1995 Schmieding et al.
5,466,229 A 11/1995 Elson et al.
5,478,334 A 12/1995 Bernstein
5,499,977 A 3/1996 Marx
5,525,407 A 6/1996 Yang
5,543,042 A 8/1996 Filan et al.
D373,928 S 9/1996 Green
5,582,604 A 12/1996 Ahr et al.
5,592,950 A 1/1997 Kopelowicz
5,593,389 A 1/1997 Chang
5,605,161 A 2/1997 Cross
5,614,699 A 3/1997 Yashiro et al.
5,618,277 A 4/1997 Goulter
5,628,735 A 5/1997 Skow
5,632,736 A 5/1997 Block
5,636,643 A 6/1997 Argenta et al.
5,637,104 A 6/1997 Ball et al.
5,641,277 A 6/1997 Gondek
D380,543 S 7/1997 Piontek et al.
5,662,633 A 9/1997 Doak et al.
5,674,212 A 10/1997 Osborn et al.
5,678,564 A 10/1997 Lawrence et al.
5,678,654 A 10/1997 Uzawa
5,681,297 A 10/1997 Hashimoto et al.
5,687,429 A 11/1997 Rahlff
5,695,485 A 12/1997 Duperret et al.
5,695,487 A 12/1997 Cohen et al.
5,700,254 A 12/1997 Mcdowall et al.
5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.

(56) References Cited

U.S. PATENT DOCUMENTS

| | | | |
|---|---|---|---|
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,859,393 | A | 1/1999 | Cummins et al. |
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 5,984,045 | A | 11/1999 | Maeda et al. |
| 6,007,524 | A | 12/1999 | Schneider |
| 6,007,526 | A | 12/1999 | Passalaqua et al. |
| D421,307 | S | 2/2000 | Harmanoglu |
| 6,039,060 | A | 3/2000 | Rower |
| 6,050,983 | A | 4/2000 | Moore et al. |
| 6,059,762 | A | 5/2000 | Boyer et al. |
| 6,061,905 | A | 5/2000 | Logic |
| 6,063,064 | A | 5/2000 | Tuckey et al. |
| 6,083,602 | A | 7/2000 | Caldwell et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,417,750 | B1 | 7/2002 | Sohn |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,526,603 | B1 | 3/2003 | Murphy |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| 6,571,910 | B2 | 6/2003 | Storm |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,848,719 | B2 | 2/2005 | Rowley |
| 6,849,065 | B2 | 2/2005 | Schmidt et al. |
| 6,857,137 | B2 | 2/2005 | Otto |
| 6,878,647 | B1 | 4/2005 | Rezai et al. |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,018,367 | B2 | 3/2006 | Nava |
| 7,066,411 | B2 | 6/2006 | Male et al. |
| 7,087,043 | B2 | 8/2006 | Dolan |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |

(56) References Cited

U.S. PATENT DOCUMENTS

| | | | |
|---|---|---|---|
| 7,699,818 | B2 | 4/2010 | Gilbert |
| 7,699,831 | B2 | 4/2010 | Bengtson et al. |
| 7,700,819 | B2 | 4/2010 | Ambrosio et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,981,087 | B2 | 7/2011 | Gesler, III |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,075,538 | B2 | 12/2011 | Vernon |
| 8,083,026 | B1 | 12/2011 | Butler |
| 8,083,094 | B2 | 12/2011 | Caulfield et al. |
| 8,128,608 | B2 | 3/2012 | Thevenin |
| 8,156,941 | B1 | 4/2012 | Simms |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,430,855 | B2 | 4/2013 | Burgess et al. |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,702,667 | B1 | 4/2014 | Johnson |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,740,852 | B2 | 6/2014 | Aviles |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,839,792 | B2 | 9/2014 | Brunner |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,415,191 | B2 | 8/2016 | Aviles |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| D806,236 | S | 12/2017 | Lin |
| 9,868,564 | B2 | 1/2018 | Mcgirr et al. |
| D814,239 | S | 4/2018 | Arora |
| D817,484 | S | 5/2018 | Lafond |
| 9,968,908 | B2 | 5/2018 | Ladrech et al. |
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |

(56) References Cited

U.S. PATENT DOCUMENTS

| | | | |
|---|---|---|---|
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Mllarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,623 | B2 | 10/2020 | VanMiddendorp et al. |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| 11,002,165 | B2 | 5/2021 | Poulin |
| D923,365 | S | 6/2021 | Wang |
| 11,020,567 | B2 | 6/2021 | Rule et al. |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,199,116 | B2 | 12/2021 | Ostromecki et al. |
| 11,207,206 | B2 | 12/2021 | Sharma et al. |
| D941,998 | S | 1/2022 | Tretheway et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,446,174 | B2 | 9/2022 | Newton |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,702,969 | B2 | 7/2023 | Bartu et al. |
| 11,806,266 | B2 | 11/2023 | Sanchez et al. |
| 11,813,189 | B2 | 11/2023 | Hussey et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,877,948 | B2 | 1/2024 | Pinlac |
| 11,890,221 | B2 | 2/2024 | Ulreich et al. |
| 11,911,160 | B2 | 2/2024 | Woodard et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| 12,048,644 | B2 | 7/2024 | Davis |
| D1,038,385 | S | 8/2024 | Ecklund et al. |
| 12,064,372 | B2 | 8/2024 | Godinez et al. |
| 12,070,432 | B2 | 8/2024 | Tourchak et al. |
| 12,090,083 | B2 | 9/2024 | Ecklund et al. |
| 12,121,468 | B2 | 10/2024 | Sanchez et al. |
| 12,133,813 | B2 | 11/2024 | Ulreich et al. |
| 12,138,195 | B2 | 11/2024 | Alder et al. |
| D1,054,019 | S | 12/2024 | Miyawaki |
| 12,161,579 | B2 | 12/2024 | Sanchez et al. |
| D1,059,585 | S | 1/2025 | Miyawaki |
| D1,059,586 | S | 1/2025 | Miyawaki |
| 12,186,229 | B2 | 1/2025 | Davis et al. |
| 12,193,962 | B2 | 1/2025 | Newton et al. |
| 12,208,031 | B2 | 1/2025 | Knapp et al. |
| 12,233,003 | B2 | 2/2025 | Newton |
| D1,067,424 | S | 3/2025 | Naughton et al. |
| 12,245,966 | B2 | 3/2025 | Newton |
| 12,257,173 | B2 | 3/2025 | Newton et al. |
| 12,274,638 | B2 | 4/2025 | Spector |
| D1,074,995 | S | 5/2025 | Laffay et al. |
| 12,324,765 | B2 | 6/2025 | Sanchez et al. |
| 12,350,190 | B2 | 7/2025 | Hughett, Sr. et al. |
| 12,447,042 | B2 | 10/2025 | Martin et al. |
| 12,465,515 | B2 | 11/2025 | Brooks |
| D1,104,255 | S | 12/2025 | Hanna et al. |
| D1,107,222 | S | 12/2025 | Ecklund et al. |
| 12,594,182 | B2 | 4/2026 | Davis et al. |
| 2001/0037097 | A1 | 11/2001 | Cheng et al. |
| 2001/0037098 | A1 | 11/2001 | Snyder |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0033200 | A1 | 3/2002 | Alex et al. |
| 2002/0042945 | A1 | 4/2002 | Sands |
| 2002/0058915 | A1 | 5/2002 | Wakabayashi |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2002/0193762 | A1 | 12/2002 | Suydam |
| 2003/0004436 | A1 | 1/2003 | Schmidt et al. |
| 2003/0018309 | A1 | 1/2003 | Breznock |
| 2003/0032931 | A1 | 2/2003 | Grundke et al. |
| 2003/0032944 | A1 | 2/2003 | Cawood |
| 2003/0073964 | A1 | 4/2003 | Palumbo et al. |
| 2003/0074724 | A1 | 4/2003 | Sands |
| 2003/0097100 | A1 | 5/2003 | Watson |
| 2003/0110868 | A1 | 6/2003 | Muller et al. |
| 2003/0120178 | A1 | 6/2003 | Heki |
| 2003/0129178 | A1 | 7/2003 | Wegman et al. |
| 2003/0132352 | A1 | 7/2003 | Weaver |
| 2003/0157859 | A1 | 8/2003 | Ishikawa |
| 2003/0178360 | A1 | 9/2003 | Haldopoulos et al. |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0002687 | A1 | 1/2004 | Burns et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0098794 | A1 | 5/2004 | Ernest et al. |
| 2004/0102753 | A1 | 5/2004 | Butler |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |

(56) References Cited

U.S. PATENT DOCUMENTS

| | | | |
|---|---|---|---|
| 2004/0147894 | A1 | 7/2004 | Mizutani et al. |
| 2004/0147895 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0181201 | A1 | 9/2004 | Mizutani et al. |
| 2004/0187200 | A1 | 9/2004 | Otto et al. |
| 2004/0191919 | A1 | 9/2004 | Unger et al. |
| 2004/0194792 | A1 | 10/2004 | Zhuang et al. |
| 2004/0200936 | A1 | 10/2004 | Opperthauser |
| 2004/0207530 | A1 | 10/2004 | Nielsen |
| 2004/0215133 | A1 | 10/2004 | Weber et al. |
| 2004/0236292 | A1 | 11/2004 | Tazoe et al. |
| 2004/0243075 | A1 | 12/2004 | Harvie |
| 2004/0254547 | A1 | 12/2004 | Okabe et al. |
| 2005/0010182 | A1 | 1/2005 | Parks et al. |
| 2005/0010197 | A1 | 1/2005 | Lau et al. |
| 2005/0033248 | A1 | 2/2005 | Machida et al. |
| 2005/0065471 | A1 | 3/2005 | Kuntz |
| 2005/0070861 | A1 | 3/2005 | Okabe et al. |
| 2005/0070862 | A1 | 3/2005 | Tazoe et al. |
| 2005/0082300 | A1 | 4/2005 | Modrell et al. |
| 2005/0097662 | A1 | 5/2005 | Leimkuhler et al. |
| 2005/0101924 | A1 | 5/2005 | Elson et al. |
| 2005/0119630 | A1 | 6/2005 | Harvie |
| 2005/0131361 | A1 | 6/2005 | Miskie |
| 2005/0137557 | A1 | 6/2005 | Swiecicki et al. |
| 2005/0137560 | A1 | 6/2005 | Mizutani et al. |
| 2005/0137561 | A1 | 6/2005 | Mizutani et al. |
| 2005/0148984 | A1 | 7/2005 | Lindsay et al. |
| 2005/0154360 | A1 | 7/2005 | Harvie |
| 2005/0177070 | A1 | 8/2005 | Levinson et al. |
| 2005/0197639 | A1 | 9/2005 | Mombrinie |
| 2005/0197645 | A1 | 9/2005 | Karpowicz et al. |
| 2005/0215969 | A1 | 9/2005 | Mizutani et al. |
| 2005/0273069 | A1 | 12/2005 | Mizutani et al. |
| 2005/0273920 | A1 | 12/2005 | Marinas |
| 2005/0277903 | A1 | 12/2005 | Mizutani et al. |
| 2005/0277904 | A1 | 12/2005 | Chase et al. |
| 2005/0279359 | A1 | 12/2005 | Leblanc et al. |
| 2006/0004332 | A1 | 1/2006 | Marx |
| 2006/0005307 | A1 | 1/2006 | Arguelles |
| 2006/0015080 | A1 | 1/2006 | Mahnensmith |
| 2006/0015081 | A1 | 1/2006 | Suzuki et al. |
| 2006/0016778 | A1 | 1/2006 | Park |
| 2006/0054384 | A1 | 3/2006 | Chen |
| 2006/0069359 | A1 | 3/2006 | Dipalma et al. |
| 2006/0079852 | A1 | 4/2006 | Bubb et al. |
| 2006/0079854 | A1 | 4/2006 | Kay et al. |
| 2006/0100596 | A1 | 5/2006 | Miskie |
| 2006/0111648 | A1 | 5/2006 | Vermaak |
| 2006/0113334 | A1 | 6/2006 | Mikhail et al. |
| 2006/0155214 | A1 | 7/2006 | Wightman |
| 2006/0166350 | A1 | 7/2006 | Lowe et al. |
| 2006/0171997 | A1 | 8/2006 | Gruenbacher et al. |
| 2006/0180566 | A1 | 8/2006 | Mataya |
| 2006/0200102 | A1 | 9/2006 | Cooper |
| 2006/0229575 | A1 | 10/2006 | Boiarski |
| 2006/0229576 | A1 | 10/2006 | Conway et al. |
| 2006/0231648 | A1 | 10/2006 | Male et al. |
| 2006/0235266 | A1 | 10/2006 | Nan |
| 2006/0235359 | A1 | 10/2006 | Marland |
| 2006/0241553 | A1 | 10/2006 | Harvie |
| 2006/0269439 | A1 | 11/2006 | White |
| 2006/0277670 | A1 | 12/2006 | Baker et al. |
| 2007/0006368 | A1 | 1/2007 | Key et al. |
| 2007/0010797 | A1 | 1/2007 | Nishtala et al. |
| 2007/0016152 | A1 | 1/2007 | Karpowicz et al. |
| 2007/0025886 | A1 | 2/2007 | Yong |
| 2007/0032765 | A1 | 2/2007 | Honda |
| 2007/0038194 | A1 | 2/2007 | Wada et al. |
| 2007/0055209 | A1 | 3/2007 | Patel et al. |
| 2007/0073252 | A1 | 3/2007 | Forgrave |
| 2007/0106177 | A1 | 5/2007 | Hama |
| 2007/0117880 | A1 | 5/2007 | Elson et al. |
| 2007/0118993 | A1 | 5/2007 | Bates |
| 2007/0135786 | A1 | 6/2007 | Schmidt et al. |
| 2007/0137718 | A1 | 6/2007 | Rushlander et al. |
| 2007/0149935 | A1 | 6/2007 | Dirico |
| 2007/0191804 | A1 | 8/2007 | Coley |
| 2007/0203464 | A1 | 8/2007 | Green et al. |
| 2007/0214553 | A1 | 9/2007 | Carromba et al. |
| 2007/0225663 | A1 | 9/2007 | Watt et al. |
| 2007/0225666 | A1 | 9/2007 | Otto |
| 2007/0225668 | A1 | 9/2007 | Otto |
| 2007/0266486 | A1 | 11/2007 | Ramirez |
| 2007/0270716 | A1 | 11/2007 | Wu et al. |
| 2007/0282309 | A1 | 12/2007 | Bengtson et al. |
| 2008/0004576 | A1 | 1/2008 | Tanaka et al. |
| 2008/0015526 | A1 | 1/2008 | Reiner et al. |
| 2008/0015527 | A1 | 1/2008 | House |
| 2008/0033386 | A1 | 2/2008 | Okabe et al. |
| 2008/0041869 | A1 | 2/2008 | Backaert |
| 2008/0077099 | A1 | 3/2008 | House |
| 2008/0091153 | A1 | 4/2008 | Harvie |
| 2008/0091158 | A1 | 4/2008 | Yang |
| 2008/0091162 | A1 | 4/2008 | Maldonado et al. |
| 2008/0114327 | A1 | 5/2008 | Barge |
| 2008/0140033 | A1 | 6/2008 | Burgess et al. |
| 2008/0167634 | A1 | 7/2008 | Kouta et al. |
| 2008/0183157 | A1 | 7/2008 | Walters |
| 2008/0200884 | A1 | 8/2008 | Perkins et al. |
| 2008/0215031 | A1 | 9/2008 | Belfort et al. |
| 2008/0234642 | A1 | 9/2008 | Patterson et al. |
| 2008/0269703 | A1 | 10/2008 | Collins et al. |
| 2008/0281282 | A1 | 11/2008 | Finger et al. |
| 2008/0287894 | A1 | 11/2008 | Van Den Heuvel et al. |
| 2008/0312550 | A1 | 12/2008 | Nishtala et al. |
| 2009/0025717 | A1 | 1/2009 | Pinel |
| 2009/0048570 | A1 | 2/2009 | Jensen |
| 2009/0056003 | A1 | 3/2009 | Ivie et al. |
| 2009/0069761 | A1 | 3/2009 | Vogel |
| 2009/0069765 | A1 | 3/2009 | Wortham |
| 2009/0120179 | A1 | 5/2009 | Nylander et al. |
| 2009/0192482 | A1 | 7/2009 | Dodge et al. |
| 2009/0199857 | A1 | 8/2009 | Peake et al. |
| 2009/0226541 | A1 | 9/2009 | Scholz et al. |
| 2009/0234312 | A1 | 9/2009 | OToole et al. |
| 2009/0247968 | A1 | 10/2009 | Brooks et al. |
| 2009/0251510 | A1 | 10/2009 | Noro et al. |
| 2009/0254040 | A1 | 10/2009 | Bierman et al. |
| 2009/0259206 | A1 | 10/2009 | Kai et al. |
| 2009/0264840 | A1 | 10/2009 | Virginio |
| 2009/0270822 | A1 | 10/2009 | Medeiros |
| 2009/0281510 | A1 | 11/2009 | Fisher |
| 2009/0283982 | A1 | 11/2009 | Thomas |
| 2009/0306610 | A1 | 12/2009 | Van Den Heuvel et al. |
| 2010/0004612 | A1 | 1/2010 | Thevenin |
| 2010/0030189 | A1 | 2/2010 | Fleming |
| 2010/0031429 | A1 | 2/2010 | Kim et al. |
| 2010/0032789 | A1 | 2/2010 | Schoen et al. |
| 2010/0058660 | A1 | 3/2010 | Williams |
| 2010/0121289 | A1 | 5/2010 | Parks et al. |
| 2010/0158168 | A1 | 6/2010 | Murthy et al. |
| 2010/0160882 | A1 | 6/2010 | Lowe |
| 2010/0174250 | A1 | 7/2010 | Hu et al. |
| 2010/0179493 | A1 | 7/2010 | Heagle et al. |
| 2010/0185168 | A1 | 7/2010 | Graauw et al. |
| 2010/0198172 | A1 | 8/2010 | Wada et al. |
| 2010/0211032 | A1 | 8/2010 | Tsai et al. |
| 2010/0234820 | A1 | 9/2010 | Tsai et al. |
| 2010/0241104 | A1 | 9/2010 | Gilbert |
| 2010/0263113 | A1 | 10/2010 | Shelton et al. |
| 2010/0310845 | A1 | 12/2010 | Bond et al. |
| 2011/0022011 | A1 | 1/2011 | Edward |
| 2011/0028920 | A1 | 2/2011 | Johannison |
| 2011/0028922 | A1 | 2/2011 | Kay et al. |
| 2011/0034889 | A1 | 2/2011 | Smith |
| 2011/0036837 | A1 | 2/2011 | Shang |
| 2011/0040267 | A1 | 2/2011 | Wada et al. |
| 2011/0040271 | A1 | 2/2011 | Rogers et al. |
| 2011/0054426 | A1 | 3/2011 | Stewart et al. |
| 2011/0060299 | A1 | 3/2011 | Wada et al. |
| 2011/0060300 | A1 | 3/2011 | Weig et al. |

(56) References Cited

U.S. PATENT DOCUMENTS

| | | | |
|---|---|---|---|
| 2011/0077495 | A1 | 3/2011 | Gilbert |
| 2011/0077606 | A1 | 3/2011 | Wilcox et al. |
| 2011/0087337 | A1 | 4/2011 | Forsell |
| 2011/0137273 | A1 | 6/2011 | Muellejans et al. |
| 2011/0145993 | A1 | 6/2011 | Rader et al. |
| 2011/0152802 | A1 | 6/2011 | Dicamillo et al. |
| 2011/0152842 | A1 | 6/2011 | Graffam et al. |
| 2011/0164147 | A1 | 7/2011 | Takahashi et al. |
| 2011/0172620 | A1 | 7/2011 | Khambatta |
| 2011/0172625 | A1 | 7/2011 | Wada et al. |
| 2011/0198904 | A1 | 8/2011 | Thomas et al. |
| 2011/0202024 | A1 | 8/2011 | Cozzens |
| 2011/0238023 | A1 | 9/2011 | Slayton |
| 2011/0240648 | A1 | 10/2011 | Tucker |
| 2011/0251572 | A1 | 10/2011 | Nishtala et al. |
| 2011/0265889 | A1 | 11/2011 | Tanaka et al. |
| 2011/0276020 | A1 | 11/2011 | Mitsui |
| 2011/0319804 | A1 | 12/2011 | Greener |
| 2012/0004079 | A1 | 1/2012 | Hyacinth |
| 2012/0029452 | A1 | 2/2012 | Roedsten |
| 2012/0035577 | A1 | 2/2012 | Tomes et al. |
| 2012/0041400 | A1 | 2/2012 | Christensen |
| 2012/0059328 | A1 | 3/2012 | Dikeman et al. |
| 2012/0066825 | A1 | 3/2012 | Birbara et al. |
| 2012/0103347 | A1 | 5/2012 | Wheaton et al. |
| 2012/0116336 | A1 | 5/2012 | Sharma et al. |
| 2012/0137420 | A1 | 6/2012 | Gordon et al. |
| 2012/0165768 | A1 | 6/2012 | Sekiyama et al. |
| 2012/0165786 | A1 | 6/2012 | Chappa et al. |
| 2012/0209216 | A1 | 8/2012 | Jensen et al. |
| 2012/0209225 | A1 | 8/2012 | Hu et al. |
| 2012/0210503 | A1 | 8/2012 | Anzivino et al. |
| 2012/0215187 | A1 | 8/2012 | Tippet et al. |
| 2012/0228055 | A1 | 9/2012 | Kato et al. |
| 2012/0233761 | A1 | 9/2012 | Huang |
| 2012/0245541 | A1 | 9/2012 | Suzuki et al. |
| 2012/0245542 | A1 | 9/2012 | Suzuki et al. |
| 2012/0245547 | A1 | 9/2012 | Wilcox et al. |
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0019374 | A1 | 1/2013 | Schwartz |
| 2013/0036544 | A1 | 2/2013 | Lee et al. |
| 2013/0045651 | A1 | 2/2013 | Esteves et al. |
| 2013/0046258 | A1 | 2/2013 | Chambers |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0211385 | A1 | 8/2013 | Lazarus |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0253528 | A1 | 9/2013 | Haffner et al. |
| 2013/0274711 | A1 | 10/2013 | O'Day |
| 2013/0292537 | A1 | 11/2013 | Dirico |
| 2013/0324954 | A1 | 12/2013 | Friedrich |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107595 | A1 | 4/2014 | Blott et al. |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0216478 | A1 | 8/2014 | Park et al. |
| 2014/0230831 | A1 | 8/2014 | Zaltsberg et al. |
| 2014/0257231 | A1 | 9/2014 | Wang et al. |
| 2014/0276501 | A1 | 9/2014 | Cisko |
| 2014/0303582 | A1 | 10/2014 | Wright et al. |
| 2014/0316381 | A1 | 10/2014 | Reglin |
| 2014/0325746 | A1 | 11/2014 | Block |
| 2014/0343516 | A1 | 11/2014 | Coulthard et al. |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0216714 | A1 | 8/2015 | Sasaki et al. |
| 2015/0238687 | A1 | 8/2015 | Novakovic et al. |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2015/0374535 | A1 | 12/2015 | Davis et al. |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte M.d. |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 | 4/2016 | Kim |
| 2016/0135792 | A1 | 5/2016 | Cai |
| 2016/0136338 | A1 | 5/2016 | Lee et al. |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0327553 | A1 | 11/2016 | Edwards et al. |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0367726 | A1 | 12/2016 | Gratzer |
| 2016/0374848 | A1 | 12/2016 | Sanchez et al. |
| 2017/0007438 | A1 | 1/2017 | Harvie |
| 2017/0014560 | A1 | 1/2017 | Minskoff et al. |
| 2017/0028110 | A1 | 2/2017 | Smith et al. |
| 2017/0042724 | A1 | 2/2017 | Ugarte |
| 2017/0042748 | A1 | 2/2017 | Griffin |
| 2017/0049605 | A1 | 2/2017 | Wisniewski |
| 2017/0100276 | A1 | 4/2017 | Joh |
| 2017/0107312 | A1 | 4/2017 | Hinayama et al. |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |
| 2017/0165405 | A1 | 6/2017 | Muser et al. |
| 2017/0189225 | A1 | 7/2017 | Voorhees et al. |
| 2017/0202692 | A1 | 7/2017 | Laniado |
| 2017/0216081 | A1 | 8/2017 | Accosta |
| 2017/0238911 | A1 | 8/2017 | Duval |
| 2017/0246026 | A1 | 8/2017 | Laniado |
| 2017/0252014 | A1 | 9/2017 | Siller Gonzalez et al. |
| 2017/0252202 | A9 | 9/2017 | Sanchez et al. |
| 2017/0266031 | A1 | 9/2017 | Sanchez et al. |
| 2017/0266658 | A1 | 9/2017 | Bruno et al. |
| 2017/0281399 | A1 | 10/2017 | Vanmiddendorp et al. |
| 2017/0281419 | A1 | 10/2017 | Pintado |
| 2017/0312116 | A1 | 11/2017 | Laniado |

(56) References Cited

U.S. PATENT DOCUMENTS

| | | | |
|---|---|---|---|
| 2017/0312405 | A1 | 11/2017 | Newton |
| 2017/0325788 | A1 | 11/2017 | Ealovega et al. |
| 2017/0333244 | A1 | 11/2017 | Laniado |
| 2017/0340489 | A1 | 11/2017 | Yamada |
| 2017/0348139 | A1 | 12/2017 | Newton et al. |
| 2017/0354532 | A1 | 12/2017 | Holt |
| 2017/0354551 | A1 | 12/2017 | Gawley et al. |
| 2017/0367873 | A1 | 12/2017 | Grannum |
| 2018/0002075 | A1 | 1/2018 | Lee |
| 2018/0008451 | A1 | 1/2018 | Stroebech |
| 2018/0008804 | A1 | 1/2018 | Laniado |
| 2018/0021218 | A1 | 1/2018 | Brosch et al. |
| 2018/0028349 | A1 | 2/2018 | Newton et al. |
| 2018/0037384 | A1 | 2/2018 | Archeny et al. |
| 2018/0049910 | A1 | 2/2018 | Newton |
| 2018/0064572 | A1 | 3/2018 | Wiltshire |
| 2018/0104131 | A1 | 4/2018 | Killian |
| 2018/0127187 | A1 | 5/2018 | Sewell |
| 2018/0149635 | A1 | 5/2018 | Abir |
| 2018/0169281 | A1 | 6/2018 | Russell et al. |
| 2018/0193215 | A1 | 7/2018 | Davies et al. |
| 2018/0200101 | A1 | 7/2018 | Su |
| 2018/0214297 | A1 | 8/2018 | Hughett et al. |
| 2018/0215649 | A1 | 8/2018 | Wada et al. |
| 2018/0221216 | A1 | 8/2018 | Benz et al. |
| 2018/0228642 | A1 | 8/2018 | Davis et al. |
| 2018/0229014 | A1 | 8/2018 | Guirguis et al. |
| 2018/0256384 | A1 | 9/2018 | Kasirye |
| 2018/0271694 | A1 | 9/2018 | Fernandez et al. |
| 2018/0280236 | A1 | 10/2018 | Ludin et al. |
| 2018/0317892 | A1 | 11/2018 | Catlin |
| 2018/0325748 | A1 | 11/2018 | Sharma et al. |
| 2019/0001029 | A1 | 1/2019 | Davie et al. |
| 2019/0001030 | A1 | 1/2019 | Braga et al. |
| 2019/0021899 | A1 | 1/2019 | Vlet |
| 2019/0029869 | A1 | 1/2019 | Huchthausen |
| 2019/0038451 | A1 | 2/2019 | Harvie |
| 2019/0046102 | A1 | 2/2019 | Kushnir et al. |
| 2019/0059938 | A1 | 2/2019 | Holsten |
| 2019/0060138 | A1 | 2/2019 | Marquez et al. |
| 2019/0091059 | A1 | 3/2019 | Gabriel |
| 2019/0100362 | A1 | 4/2019 | Meyers et al. |
| 2019/0133126 | A1 | 5/2019 | Modak et al. |
| 2019/0133814 | A1 | 5/2019 | Tammen et al. |
| 2019/0142624 | A1 | 5/2019 | Sanchez et al. |
| 2019/0224036 | A1 | 7/2019 | Sanchez et al. |
| 2019/0226189 | A1 | 7/2019 | Braxton |
| 2019/0240079 | A1 | 8/2019 | Tuli |
| 2019/0247222 | A1 | 8/2019 | Ecklund et al. |
| 2019/0247223 | A1 | 8/2019 | Brun et al. |
| 2019/0247623 | A1 | 8/2019 | Helm et al. |
| 2019/0282391 | A1 | 9/2019 | Johannes et al. |
| 2019/0314189 | A1 | 10/2019 | Acosta |
| 2019/0314190 | A1 | 10/2019 | Sanchez et al. |
| 2019/0321587 | A1 | 10/2019 | Mcmenamin et al. |
| 2019/0344934 | A1 | 11/2019 | Faerber et al. |
| 2019/0358372 | A1 | 11/2019 | Askem et al. |
| 2019/0365303 | A1 | 12/2019 | Bullington et al. |
| 2019/0365307 | A1 | 12/2019 | Laing et al. |
| 2019/0365561 | A1 | 12/2019 | Newton et al. |
| 2019/0374373 | A1 | 12/2019 | Joh |
| 2020/0008985 | A1 | 1/2020 | Nguyen et al. |
| 2020/0016012 | A1 | 1/2020 | Dutkiewicz |
| 2020/0030595 | A1 | 1/2020 | Boukidjian et al. |
| 2020/0040561 | A1 | 2/2020 | Sugawara |
| 2020/0046544 | A1 | 2/2020 | Godinez et al. |
| 2020/0055638 | A1 | 2/2020 | Lau et al. |
| 2020/0070392 | A1 | 3/2020 | Huber et al. |
| 2020/0085609 | A1 | 3/2020 | Schelch et al. |
| 2020/0085610 | A1 | 3/2020 | Cohn et al. |
| 2020/0086090 | A1 | 3/2020 | Von Weymarn-schärli et al. |
| 2020/0107518 | A1 | 4/2020 | Hiroshima et al. |
| 2020/0129322 | A1 | 4/2020 | Leuckel |
| 2020/0171217 | A9 | 6/2020 | Braga et al. |
| 2020/0179177 | A1 | 6/2020 | Erdem et al. |
| 2020/0187918 | A1 | 6/2020 | Wiygul |
| 2020/0206015 | A1 | 7/2020 | Langer |
| 2020/0206039 | A1 | 7/2020 | Mclain |
| 2020/0214910 | A1 | 7/2020 | Varona et al. |
| 2020/0216898 | A1 | 7/2020 | Hubbell |
| 2020/0216989 | A1 | 7/2020 | Kinugasa et al. |
| 2020/0229964 | A1 | 7/2020 | Staali et al. |
| 2020/0231343 | A1 | 7/2020 | Freedman et al. |
| 2020/0232841 | A1 | 7/2020 | Satish et al. |
| 2020/0246172 | A1 | 8/2020 | Ho |
| 2020/0246203 | A1 | 8/2020 | Tulk et al. |
| 2020/0255189 | A1 | 8/2020 | Liu |
| 2020/0261280 | A1 | 8/2020 | Heyman |
| 2020/0276046 | A1 | 9/2020 | Staali et al. |
| 2020/0306075 | A1 | 10/2020 | Newton et al. |
| 2020/0315837 | A1 | 10/2020 | Radl et al. |
| 2020/0315838 | A1 | 10/2020 | Eckert |
| 2020/0315872 | A1 | 10/2020 | Viens et al. |
| 2020/0315874 | A1 | 10/2020 | Viens et al. |
| 2020/0331672 | A1 | 10/2020 | Bertram et al. |
| 2020/0345332 | A1 | 11/2020 | Duval |
| 2020/0352774 | A1 | 11/2020 | Rabinowitz et al. |
| 2020/0353135 | A1 | 11/2020 | Gregory et al. |
| 2020/0367677 | A1 | 11/2020 | Silsby et al. |
| 2020/0369444 | A1 | 11/2020 | Silsby et al. |
| 2020/0375781 | A1 | 12/2020 | Staali et al. |
| 2020/0375810 | A1 | 12/2020 | Carlin et al. |
| 2020/0384242 | A1 | 12/2020 | Havard et al. |
| 2020/0385179 | A1 | 12/2020 | Mccourt |
| 2020/0390591 | A1 | 12/2020 | Glithero et al. |
| 2020/0390592 | A1 | 12/2020 | Merrill |
| 2020/0398024 | A1 | 12/2020 | Fletter et al. |
| 2020/0405521 | A1 | 12/2020 | Glasroe |
| 2020/0405523 | A1 | 12/2020 | Obst et al. |
| 2021/0007910 | A1 | 1/2021 | Furukawa |
| 2021/0008771 | A1 | 1/2021 | Huber et al. |
| 2021/0009323 | A1 | 1/2021 | Markarian et al. |
| 2021/0020072 | A1 | 1/2021 | Moehring et al. |
| 2021/0023279 | A1 | 1/2021 | Radl et al. |
| 2021/0059853 | A1 | 3/2021 | Davis et al. |
| 2021/0061523 | A1 | 3/2021 | Bytheway |
| 2021/0069005 | A1 | 3/2021 | Sanchez et al. |
| 2021/0069008 | A1 | 3/2021 | Blabas et al. |
| 2021/0069009 | A1 | 3/2021 | Im |
| 2021/0069030 | A1 | 3/2021 | Nishikawa et al. |
| 2021/0077993 | A1 | 3/2021 | Nazareth et al. |
| 2021/0113749 | A1 | 4/2021 | Radl et al. |
| 2021/0121318 | A1 | 4/2021 | Pinlac |
| 2021/0137724 | A1 | 5/2021 | Ecklund et al. |
| 2021/0138190 | A1 | 5/2021 | Erbey et al. |
| 2021/0154055 | A1 | 5/2021 | Mllarreal |
| 2021/0170079 | A1 | 6/2021 | Radl et al. |
| 2021/0178390 | A1 | 6/2021 | Oueslati et al. |
| 2021/0186742 | A1 | 6/2021 | Newton et al. |
| 2021/0186744 | A1 | 6/2021 | Spector |
| 2021/0206144 | A1 | 7/2021 | Ewell |
| 2021/0211568 | A1 | 7/2021 | Zhou et al. |
| 2021/0212865 | A1 | 7/2021 | Wallajapet et al. |
| 2021/0220162 | A1 | 7/2021 | Jamison |
| 2021/0220163 | A1 | 7/2021 | Mayrand |
| 2021/0228400 | A1 | 7/2021 | Glithero |
| 2021/0228401 | A1 | 7/2021 | Becker et al. |
| 2021/0228795 | A1 | 7/2021 | Hughett et al. |
| 2021/0229877 | A1 | 7/2021 | Ragias et al. |
| 2021/0236323 | A1 | 8/2021 | Austermann et al. |
| 2021/0236324 | A1 | 8/2021 | Sweeney |
| 2021/0251814 | A1 | 8/2021 | Jönegren et al. |
| 2021/0267787 | A1 | 9/2021 | Nazemi |
| 2021/0275343 | A1 | 9/2021 | Sanchez et al. |
| 2021/0275344 | A1 | 9/2021 | Wing |
| 2021/0290454 | A1 | 9/2021 | Yamada |
| 2021/0290464 | A1 | 9/2021 | Furuta |
| 2021/0315726 | A1 | 10/2021 | Lin |
| 2021/0315727 | A1 | 10/2021 | Jiang |
| 2021/0353449 | A1 | 11/2021 | Sharma et al. |
| 2021/0353450 | A1 | 11/2021 | Sharma et al. |
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |

(56) References Cited

U.S. PATENT DOCUMENTS

| | | | |
|---|---|---|---|
| 2021/0393433 | A1 | 12/2021 | Godinez et al. |
| 2022/0015958 | A1 | 1/2022 | Ito |
| 2022/0023091 | A1 | 1/2022 | Ecklund et al. |
| 2022/0026546 | A1 | 1/2022 | Aono et al. |
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1 | 7/2022 | Levin et al. |
| 2022/0241106 | A1 | 8/2022 | Johannes et al. |
| 2022/0241115 | A1 | 8/2022 | Lang et al. |
| 2022/0247407 | A1 | 8/2022 | Yamamoto et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287691 | A1 | 9/2022 | Wormser et al. |
| 2022/0287867 | A1 | 9/2022 | Jones et al. |
| 2022/0287868 | A1 | 9/2022 | Garvey et al. |
| 2022/0296406 | A1 | 9/2022 | Keelen |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Yin et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0000617 | A1 | 1/2024 | Locke |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0164937 | A1 | 5/2024 | Gloeckner et al. |
| 2024/0180737 | A1 | 6/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0335599 | A1 | 10/2024 | Cheng et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0017761 | A1 | 1/2025 | Lee |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |
| 2026/0020972 | A1 | 1/2026 | Godinez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |

(56) References Cited

FOREIGN PATENT DOCUMENTS

| | | | |
|---|---|---|---|
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 2569779 | Y | 9/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 105616072 | A | 6/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 207785556 | U | 8/2018 |
| CN | 110171118 | A | 8/2019 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 112384178 | A | 2/2021 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 3104356 | A1 | 9/1982 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 202006018506 | U1 | 3/2007 |
| DE | 102011103783 | A1 | 12/2012 |
| DE | 102012112818 | A1 | 6/2014 |
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0945231 | A2 | 9/1999 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2294812 | A1 | 7/1976 |
| FR | 2826704 | A1 | 1/2003 |
| GB | 871820 | A | 7/1961 |
| GB | 0873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |

(56) References Cited

FOREIGN PATENT DOCUMENTS

| | | | |
|---|---|---|---|
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022536986 | A | 8/2022 |
| JP | 2022540178 | A | 9/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20100137210 | A | 12/2010 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 200486827 | Y1 | 7/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |

(56) References Cited

FOREIGN PATENT DOCUMENTS

| | | | |
|---|---|---|---|
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |

(56) References Cited

FOREIGN PATENT DOCUMENTS

| | | | |
|---|---|---|---|
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 17/051,585 mailed Oct. 8, 2024.

Advisory Action for U.S. Appl. No. 17/446,256 mailed Nov. 19, 2024.

Advisory Action for U.S. Appl. No. 17/446,654 mailed Feb. 28, 2025.

Advisory Action for U.S. Appl. No. 17/595,747 mailed Mar. 17, 2025.

Advisory Action for U.S. Appl. No. 17/597,673 mailed Jan. 7, 2025.

Advisory Action for U.S. Appl. No. 17/653,137 mailed Nov. 20, 2024.

Advisory Action for U.S. Appl. No. 17/653,920 mailed Oct. 28, 2024.

Advisory Action for U.S. Appl. No. 17/655,464 mailed Feb. 25, 2025.

Advisory Action for U.S. Appl. No. 18/003,029 mailed Jan. 8, 2025.

Advisory Action for U.S. Appl. No. 18/134,857 mailed Oct. 23, 2024.

Advisory Action for U.S. Appl. No. 18/164,800 mailed Jan. 8, 2025.

Corrected Notice of Allowability for U.S. Appl. No. 17/450,864 mailed Oct. 24, 2024.

(56) References Cited

OTHER PUBLICATIONS

Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 18/134,857 mailed Mar. 14, 2025.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,345 mailed Feb. 6, 2025.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,408 mailed Mar. 24, 2025.
Final Office Action for U.S. Appl. No. 17/597,673 mailed Oct. 22, 2024.
Final Office Action for U.S. Appl. No. 17/625,941 mailed Feb. 18, 2025.
Final Office Action for U.S. Appl. No. 17/653,137 mailed Aug. 7, 2024.
Final Office Action for U.S. Appl. No. 17/653,314 mailed Jan. 30, 2025.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 17/757,311 mailed Mar. 31, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
International Search Report and Written Opinion from International Application No. PCT/US2023/031432 mailed Feb. 29, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
International Search Report and Written Opinion from International Application No. PCT/US2024/053681 mailed Jan. 27, 2025.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 16/478,180 mailed Mar. 5, 2025.
Issue Notification for U.S. Appl. No. 17/051,585 mailed Mar. 26, 2025.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/646,771 mailed Mar. 19, 2025.
Issue Notification for U.S. Appl. No. 17/661,090 maiiled Feb. 5, 2025.
Issue Notification for U.S. Appl. No. 17/662,700 mailed Oct. 23, 3024.
Issue Notification for U.S. Appl. No. 17/663,330 mailed Feb. 26, 2025.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/140,751 mailed Feb. 12, 2025.
Issue Notification for U.S. Appl. No. 18/198,464 mailed Nov. 20, 2024.
Issue Notification for U.S. Appl. No. 18/389,009 mailed Dec. 18, 2024.
Issue Notification for U.S. Appl. No. 18/426,795 mailed Feb. 19, 2025.
Non-Final Office Action for U.S. Appl. No. 16/433,773 mailed Feb. 28, 2025.
Non-Final Office Action for U.S. Appl. No. 16/478,180 mailed Aug. 7, 2024.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/451,345 mailed Jul. 25, 2024.
Non-Final Office Action for U.S. Appl. No. 17/451,354 mailed Mar. 19, 2025.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/631,619 mailed Mar. 19, 2025.
Non-Final Office Action for U.S. Appl. No. 17/645,821 mailed Mar. 31, 2025.

(56) References Cited

OTHER PUBLICATIONS

Non-Final Office Action for U.S. Appl. No. 17/645,821 mailed Sep. 6, 2024.
Non-Final Office Action for U.S. Appl. No. 17/653, 137 mailed Jan. 28, 2025.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/655,464 mailed Mar. 20, 2025.
Non-Final Office Action for U.S. Appl. No. 17/749,340 mailed Aug. 14, 2024.
Non-Final Office Action for U.S. Appl. No. 17/754,736 mailed Mar. 31, 2025.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/907,125 mailed Dec. 13, 2024.
Non-Final Office Action for U.S. Appl. No. 17/996,064 mailed Mar. 6, 2025.
Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/444,792 mailed Mar. 28, 2025.
Notice of Allowance for U.S. Appl. No. 17/447,123 mailed Jul. 26, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/596,629 mailed Jan. 29, 2025.
Notice of Allowance for U.S. Appl. No. 17/597,673 mailed Feb. 26, 2025.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 17/749,340 mailed Feb. 14, 2025.
Notice of Allowance for U.S. Appl. No. 17/758,316 mailed Mar. 24, 2025.
Notice of Allowance for U.S. Appl. No. 17/996,155 mailed Mar. 11, 2025.
Notice of Allowance for U.S. Appl. No. 18/134,857 mailed Feb. 20, 2025.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Restriction Requirement for U.S. Appl. No. 17/929,887 mailed Mar. 10, 2025.
U.S. Appl. No. 17/013,822, filed Sep. 7, 2020.
U.S. Appl. No. 18/728,604, filed Jul. 12, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.

(56) References Cited

OTHER PUBLICATIONS

U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 63,564,696, filed Mar. 13, 2024.
U.S. Appl. No. 63/181,709, filed Apr. 29, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
Advisory Action for U.S. Appl. No. 16/905,400 mailed Feb. 16, 2022.
Corrected Notice of Allowability for U.S. Appl. No. 17/330,657 mailed Dec. 9, 2021.
International Search Report and Written Opinion from International Application No. PCT/US2021/045188 mailed Jan. 26, 2022.
Non-Final Office Action for U.S. Appl. No. 16/245,726 mailed Jan. 21, 2022.
Non-Final Office Action for U.S. Appl. No. 29/741,751 mailed Jan. 18, 2022.
Notice of Allowance for U.S. Appl. No. 17/088,272 mailed Nov. 24, 2021.
Notice of Allowance for U.S. Appl. No. 17/330,657 mailed Nov. 26, 2021.
Restriction Requirement for U.S. Appl. No. 16/433,773 mailed Dec. 7, 2021.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/646,771, filed Jan. 3, 2022.
U.S. Appl. No. 17/655,464, filed Mar. 18, 2022.
U.S. Appl. No. 62/935,337, filed Nov. 14, 2019.
U.S. Appl. No. 63/138,878, filed Jan. 19, 2021.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.

(56) References Cited

OTHER PUBLICATIONS

International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.

(56) References Cited

OTHER PUBLICATIONS

Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 14/433,773, filed Apr. 3, 2020.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/645,821, filed Dec. 23, 2021.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.

(56) References Cited

OTHER PUBLICATIONS

U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and U.S. Pat. No. 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and U.S. Pat. No. 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and U.S. Pat. No. 10,390,989, May 29, 2020, 193 pages.
Defendant and Counterclaim Plaintiff Sage Products, LLC's Answer, Defenses, and Counterclaims To Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology 2005-06", British Department of Health, Nov. 2006, 40 pages.
"Step by Step How Ur24 WorksHome", http://medicalpatentur24.com, Aug. 30, 2017, 4 pages.
"Underwear that absorbs your period", Thinx!, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, 2014, 4 pages.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , Female Urinary and Pouch and Male Urinary Pouch Brochure, 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.

(56) References Cited

OTHER PUBLICATIONS

Karp , et al., “Dry solution to a sticky problem”, Nature., 2011, pp. 42-43.
Lee , et al., “Continuous Fabrication of Wide-Tip Microstructures for Bio-Inspired Dry Adhesives via Tip Inking Process”, Journal of Chemistry, Jan. 2, 2019, pp. 1-5.
MaCaulay , et al., “A Noninvasive Continence Management System: Development and Evaluation of a Novel Toileting Device for Women”, The Wound, Ostomy and Continence Nurses Society, 2007, pp. 641-648.
Newman , et al., “The Urinary Incontinence Sourcebook”, Petition for Interparties Review, 1997, 23 pages.
Newton , et al., “Measuring Safety, Effectiveness and Ease of Use of PureWick in the Management of Urinary Incontinence in Bedbound Women: Case Studies”, Jan. 8, 2016, 11 pages.
Parmar , “10 Finalists Chosen for Dare-to-Dream Medtech Design Challenge (PureWick)”, Design Services, Nov. 10, 2014, 3 pages.
Parness , et al., “A microfabricated wedge-shaped adhesive array displaying gecko-like dynamic adhesion, directionality”, J.R. Soc. Interface, 2009, pp. 1223-1232.
Purewick , “Incontinence Relief for Women”, Presentation, Sep. 23, 2015, 7 pages.
Pytlik , “Super Absorbent Polymers”, University of Buffalo.
Sachtman , “New Relief for Pilots? It Depends”, Wired, 2008, 2 pages.
Tsipenyuk , et al., “Use of biomimetic hexagonal surface texture in friction against lubricated skin”, Journal of The Royal Society—Interface, 2014, pp. 1-6.
Advisory Action for U.S. Appl. No. 16/452,258 mailed Oct. 26, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
International Search Report and Written Opinion from International Application No. PCT/IB2021/057173 mailed Nov. 5, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/060993 mailed Mar. 18, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015420 mailed Nov. 18, 2022.
International Search Report and Written Opinion from International Application No. PCT/US2022/015492 mailed Apr. 26, 2022.
International Search Report and Written Opinion from International Application No. PCT/US2022/018170 mailed May 31, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
Issue Notification for U.S. Appl. No. 16,905,400 mailed Nov. 30, 2022.
Non-Final Office Action for U.S. Appl. No. 16/905,400 mailed Apr. 27, 2022.
Non-Final Office Action for U.S. Appl. No. 17/451,345 mailed Dec. 7, 2022.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/905,400 mailed Aug. 17, 2022.
Notice of Allowance for U.S. Appl. No. 17/461,036 mailed Oct. 6, 2022.
Notice of Allowance for U.S. Appl. No. 29/741,751 mailed Jun. 9, 2022.
U.S. Appl. No. 17/657,474, filed Mar. 31, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/996,064, filed Oct. 12, 2022.
U.S. Appl. No. 17/996,253, filed Oct. 14, 2022.
U.S. Appl. No. 17/996,556, filed Oct. 19, 2022.
U.S. Appl. No. 62/923,279, filed Oct. 18, 2019.
U.S. Appl. No. 62/967,158, filed Jan. 26, 2020.
U.S. Appl. No. 63/094,646, filed Oct. 21, 2020.
U.S. Appl. No. 63/191,558, filed May 21, 2021.
U.S. Appl. No. 63/208,262, filed Jun. 8, 2021.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 16/904,868 mailed Jun. 15, 2022.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.

(56) References Cited

OTHER PUBLICATIONS

Advisory Action for U.S. Appl. No. 17/451,345 mailed Jul. 3, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Mar. 10, 2022.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/051456 mailed Jan. 19, 2022.
International Search Report and Written Opinion from International Application No. PCT/US2021/056566 mailed Feb. 11, 2022.

(56) References Cited

OTHER PUBLICATIONS

International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015471 mailed May 16, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/245,726 mailed Oct. 18, 2023.
Issue Notification for U.S. Appl. No. 16/449,039 mailed Jun. 19, 2024.
Issue Notification for U.S. Appl. No. 16/899,956 mailed Mar. 29, 2023.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 17/448,811 mailed Jul. 3, 2024.
Issue Notification for U.S. Appl. No. 17/461,036 mailed Oct. 11, 2023.
Issue Notification for U.S. Appl. No. 17/657,474 mailed Jun. 19, 2024.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/452,258 mailed Jun. 20, 2024.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.

(56) References Cited

OTHER PUBLICATIONS

Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/378,015 mailed Jul. 5, 2024.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/661,090 mailed May 22, 2024.
Non-Final Office Action for U.S. Appl. No. 17/662,700 mailed Jul. 22, 2022.
Non-Final Office Action for U.S. Appl. No. 17/663,330 mailed Jul. 1, 2024.
Non-Final Office Action for U.S. Appl. No. 17/663,330 mailed Jun. 29, 2023.
Non-Final Office Action for U.S. Appl. No. 17/664,487 mailed Jun. 17, 2024.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Notice of Allowance for U.S. Appl. No. 16/245,726 mailed Jul. 6, 2023.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/088,272 mailed Mar. 4, 2022.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/330,657 mailed Mar. 16, 2022.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.

(56) References Cited

OTHER PUBLICATIONS

Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Jun. 12, 2024.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/527,769 mailed Jun. 17, 2024.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/384,196, filed Dec. 19, 2016.
U.S. Appl. No. 17/444,792, filed Aug. 10, 2021.
U.S. Appl. No. 17/451,719, filed Oct. 19, 2021.
U.S. Appl. No. 17/653,314, filed Mar. 3, 2022.
U.S. Appl. No. 17/653,920, filed Mar. 8, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,155, filed Oct. 13, 2022.
U.S. Appl. No. 17/996,468, filed Oct. 18, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/757,964, filed Jun. 28, 2024.
U.S. Appl. No. 18/758,025, filed Jun. 28, 2024.
U.S. Appl. No. 62/926,767, filed Oct. 28, 2019.
U.S. Appl. No. 62/991,754, filed Mar. 19, 2020.
U.S. Appl. No. 63/008,112, filed Apr. 10, 2020.
U.S. Appl. No. 63/150,640, filed Feb. 18, 2021.
U.S. Appl. No. 63/192,289, filed May 24, 2021.
U.S. Appl. No. 63/230,897, filed Aug. 9, 2021.
U.S. Appl. No. 63/241,328, filed Sep. 7, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.

(56) References Cited

OTHER PUBLICATIONS

"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Oblong", Cambridge Dictionary, https://dictionary.cambridge.org/dictionary/english/oblong, 2024, 1 page.
"Revised AMXDmax Advanced Mission Extender Device User & Maintenance Guide", Omni Medical Systems, Oct. 8, 2019, 52 pages.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
"Proximate Definition & Meaning" <https://www.merriam-webster.com/dictionary/> 2025.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 16/452,258 mailed Apr. 17, 2026.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Apr. 16, 2026.
Advisory Action for U.S. Appl. No. 17/451,345 mailed May 13, 2025.
Advisory Action for U.S. Appl. No. 17/653,314 mailed Apr. 8, 2025.
Advisory Action for U.S. Appl. No. 17/664,487 mailed Apr. 24, 2025.
Advisory Action for U.S. Appl. No. 17/664,487 mailed Apr. 9, 2026.
Advisory Action for U.S. Appl. No. 17/757,311 mailed Jul. 2, 2025.
Advisory Action for U.S. Appl. No. 17/929,887 mailed Apr. 16, 2026.
Advisory Action for U.S. Appl. No. 18/006,807 mailed May 4, 2026.
Advisory Action for U.S. Appl. No. 18/042,842 mailed Apr. 14, 2026.
Advisory Action for U.S. Appl. No. 18/164,800 mailed Apr. 9, 2026.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Application No. 18/041,109 mailed Apr. 2, 2026.
Corrected Notice of Allowability for U.S. Appl. No. 18/249,577 mailed Apr. 15, 2026.
Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/595,747 mailed Feb. 19, 2026.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/628,411 mailed Apr. 7, 2026.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/758,152 mailed Apr. 7, 2026.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.

(56) References Cited

OTHER PUBLICATIONS

Final Office Action for U.S. Appl. No. 17/907,125 mailed Apr. 30, 2025.
Final Office Action for U.S. Appl. No. 17/929,887 mailed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/115,444 mailed May 19, 2026.
Final Office Action for U.S. Appl. No. 18/139,523 mailed May 8, 2025.
Final Office Action for U.S. Appl. No. 18/150,360 mailed Apr. 10, 2026.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/254,638 mailed Apr. 8, 2026.
Final Office Action for U.S. Appl. No. 18/265,736 mailed Dec. 1, 2025.
Final Office Action for U.S. Appl. No. 18/548,152 mailed Apr. 15, 2026.
Final Office Action for U.S. Appl. No. 18/556,945 mailed May 29, 2026.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
International Search Report and Written Opinion from International Application No. PCT/US2025/035383 mailed Oct. 10, 2025.
Issue Notification for U.S. Appl. No. 16/433,773 mailed Jan. 21, 2026.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,600 mailed Apr. 29, 2026.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/645,821 mailed Apr. 1, 2026.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/759,697 mailed May 6, 2026.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/584,002 mailed Apr. 16, 2025.
Non-Final Office Action for U.S. Appl. No. 16/452,258 mailed Sep. 24, 2025.
Non-Final Office Action for U.S. Appl. No. 17/378,015 mailed Dec. 12, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/446,654 mailed May 14, 2026.
Non-Final Office Action for U.S. Appl. No. 17/595,747 mailed Jun. 12, 2025.
Non-Final Office Action for U.S. Appl. No. 17/597,408 mailed Apr. 7, 2026.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/635,866 mailed Jul. 29, 2025.
Non-Final Office Action for U.S. Appl. No. 17/653,314 mailed May 8, 2025.
Non-Final Office Action for U.S. Appl. No. 17/664,487 mailed May 19, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Sep. 17, 2025.

(56) References Cited

OTHER PUBLICATIONS

Non-Final Office Action for U.S. Appl. No. 17/809,083 mailed May 21, 2026.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/003,029 mailed Apr. 20, 2026.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 1, 2026.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,391 mailed Apr. 29, 2026.
Non-Final Office Action for U.S. Appl. No. 18/260,394 mailed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/294,403 mailed May 15, 2026.
Non-Final Office Action for U.S. Appl. No. 18/335,579 mailed Apr. 24, 2026.
Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/549,658 mailed May 29, 2026.
Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/569,778 mailed May 1, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 18/757,964 mailed Mar. 27, 2026.
Non-Final Office Action for U.S. Appl. No. 18/834,176 mailed May 18, 2026.
Non-Final Office Action for U.S. Appl. No. 18/835,068 mailed May 19, 2026.
Non-Final Office Action for U.S. Appl. No. 18/835,444 mailed Apr. 24, 2026.
Non-Final Office Action for U.S. Appl. No. 19/237,368 mailed Apr. 6, 2026.
Non-Final Office Action for U.S. Appl. No. 19/353,151 mailed May 15, 2026.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed May 27, 2025.
Notice of Allowance for U.S. Appl. No. 17/614,173 mailed May 7, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.

(56) References Cited

OTHER PUBLICATIONS

Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/757,311 mailed May 5, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/246,121 mailed May 12, 2026.
Notice of Allowance for U.S. Appl. No. 18/249,577 mailed Mar. 31, 2026.
Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/264,278 mailed Apr. 24, 2026.
Notice of Allowance for U.S. Appl. No. 18/294,370 mailed Mar. 17, 2026.
Notice of Allowance for U.S. Appl. No. 18/553,625 mailed Apr. 15, 2026.
Notice of Allowance for U.S. Appl. No. 18/558,502 mailed May 6, 2026.
Notice of Allowance for U.S. Appl. No. 18/610,523 mailed Mar. 4, 2026.
Restriction Requirement for U.S. Appl. No. 17/755,236 mailed Apr. 24, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,368 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 18/546,465, filed Aug. 15, 2023.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151 filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150 filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100 filed Feb. 25, 2026.
U.S. Appl. No. 19/534,156 filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.

(56) References Cited

OTHER PUBLICATIONS

U.S. Appl. No. 19/544,501, filed Feb. 19, 2026.
U.S. Appl. No. 19/554,125 filed Mar. 2, 2026.
U.S. Appl. No. 19/579,050, filed Apr. 16, 2026.
U.S. Appl. No. 19/582,525, filed Apr. 28, 2026.
U.S. Appl. No. 19/584,751, filed May 5, 2026.
U.S. Appl. No. 19/584,819, filed May 5, 2026.
U.S. Appl. No. 19/588,736 mailed May 19, 2026.
U.S. Appl. No. 19/638,741, filed Apr. 3, 2026.
U.S. Appl. No. 19/657,823, filed Apr. 24, 2026.
U.S. Appl. No. 62/665,711, filed May 2, 2018.

* cited by examiner

FLUID COLLECTION DEVICES, SYSTEMS AND METHODS

CROSS-REFERENCE TO RELATED APPLICATIONS

This Application is a U.S. Nationalization of PCT International Application No. PCT/US2020/041242 filed on 8 Jul. 2020, which claims priority to U.S. Patent Application No. 62/873,045 filed 11 Jul. 2019, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to fluid collection devices and methods of using fluid collection devices. In an embodiment, a fluid collection device is disclosed. The fluid collection device includes at least one wicking material including an outer surface. The fluid collection device includes a fluid impermeable coating adhered to at least a portion of the outer surface of the at least one wicking material, the fluid impermeable coating defining a chamber within the fluid collection device partially enclosing the at least one wicking material and a defining an opening through which a portion of the at least one wicking material is exposed, the opening configured to be positioned adjacent to a female urethra or have a male urethra positioned therethrough In an embodiment, a fluid collection system is disclosed. The fluid collection system includes a fluid storage container configured to hold a fluid. The fluid collection system includes a fluid collection device including at least one wicking material including an outer surface. The fluid collection device includes a fluid impermeable coating adhered to at least a portion of an outer surface of the at least one wicking material, the fluid impermeable coating defining a chamber within the fluid collection device and an opening through which a portion of the at least one wicking material is exposed, the opening configured to be positioned adjacent to a female urethra or have a male urethra positioned therethrough. The fluid collection system includes a conduit disposed within the chamber, the conduit including an inlet positioned within the chamber and an outlet configured to be fluidly coupled to a vacuum source. The fluid collection system includes a vacuum source fluidly coupled to one or more of the fluid storage container or the outlet of the fluid collection device, the vacuum source configured to draw fluid from the fluid collection device.

In an embodiment, a method to collect fluid is disclosed. The method includes positioning an opening of a fluid collection device adjacent to a female urethra or around a male urethra of a user, the opening defined by a fluid impermeable coating of the fluid collection device. The method includes receiving fluid from the female urethra or male urethra into a chamber of the fluid collection device, the chamber of the fluid collection device at least partially defined by the fluid impermeable coating.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
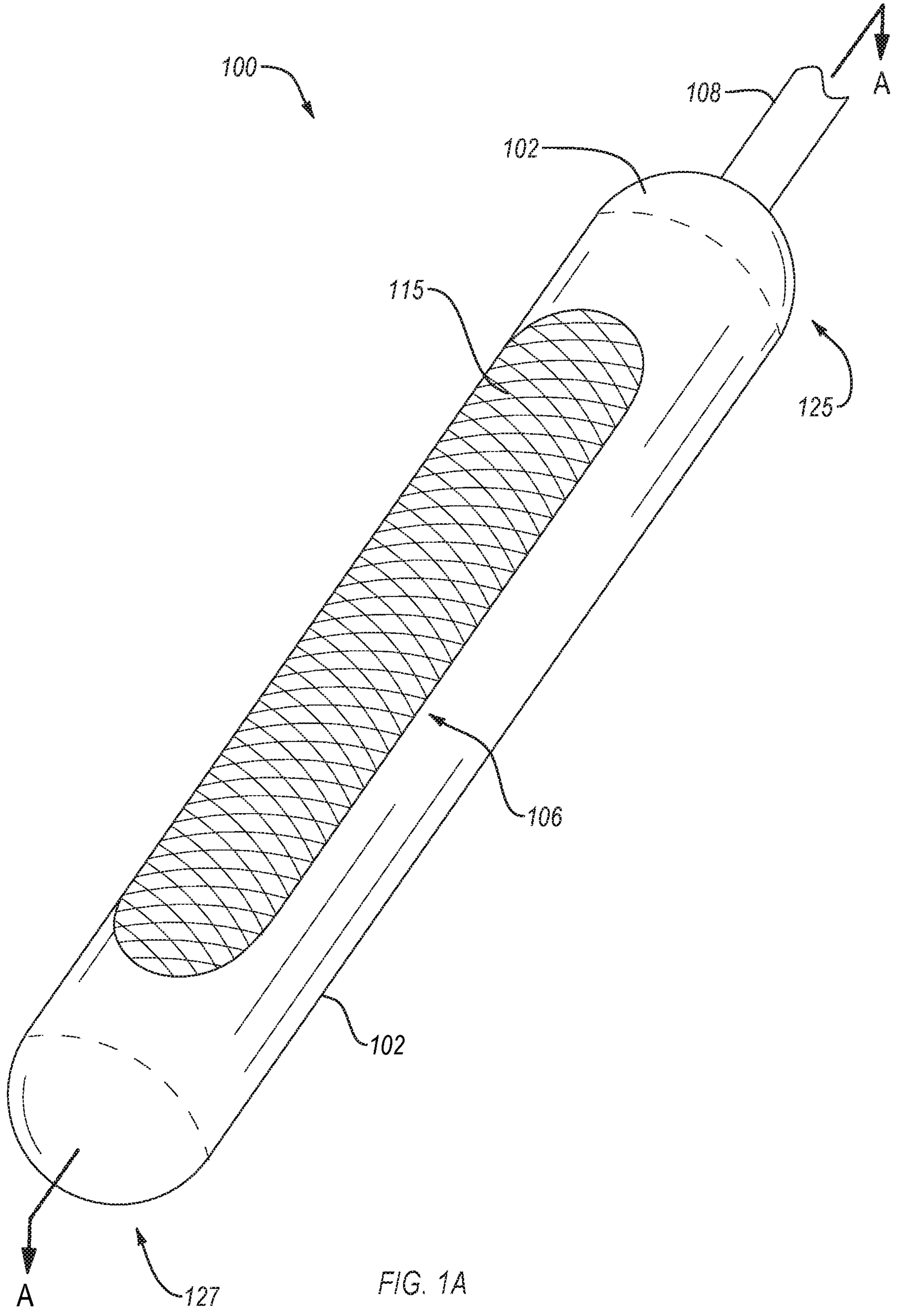
FIG. 1A is an isometric view of a fluid collection device, according to an embodiment.

Embodiments disclosed herein are related to fluid collection devices and methods of using the same. The devices and systems disclosed herein are configured to collect fluids from an individual. The fluids collected by the fluid collection devices may include at least one of urine, vaginal discharge, penile discharge, reproductive fluids, blood, sweat, or other bodily fluids.

The fluid collection devices include wicking material having a fluid impermeable coating that at least partially defines a chamber therein. The fluid impermeable coating also defines an opening extending therethrough that is configured to be positioned adjacent to a female urethra or have a male urethra positioned therethrough. The fluid collection device also includes a conduit having a channel extending between an inlet and outlet thereof. The inlet is fluidly coupled to the chamber and the outlet is configured to be fluidly coupled to a fluid storage (vessel or container)

or vacuum. The fluid impermeable coatings and fluid collection devices utilizing the coatings disclosed herein provide a soft, comfortable, and relatively smooth feel for the wearer, even on sensitive areas of the anatomy and under moist conditions.

Some conventional fluid collection devices may have a fluid impermeable shell defining an outer surface of the device. The fluid impermeable shell often includes a material that has a thickness that can create discontinuities on the surface of the device or has a relatively higher material hardness or texture than the absorbing material enclosed therein. In some instances, a conventional fluid impermeable shell may have shape, thickness, and/or material composition differences (e.g., transitions from hard to soft materials) that can create cusps, ridges, or other geometric features at the outer surface of the fluid collection device. These features may create discomfort on the skin of a wearer during use, especially prolonged use (e.g., more than an hour). For example, the transition from fluid impermeable shell material to the absorbing material therein may provide a lip or other discontinuity that creates discomfort or even sores on the skin of the wearer over time. Similarly, relatively stiffer materials in the shell may not yield to pressure exerted thereon by the skin of a wearer. Such stiffer materials may also result in discomfort or sores during prolonged use.

The fluid collection devices disclosed herein have fluid impermeable coating with one or more of a thickness, compliance, material make-up, and lack of surface features sufficient to provide a smooth comfortable feel to the wearer of the fluid collection device, even after long periods of use. For example, the fluid impermeable coating is thin enough so as not to provide a rigid or hard surface against the skin of a wearer. The fluid impermeable coating is thin enough to comply to pressure asserted thereon and provide a surface that provides little to no cusps or discontinuities. For example, the relatively thin fluid impermeable coatings disclosed herein do not create a discontinuity when transitioning from the fluid impermeable coating to the wicking material in the opening. Accordingly, the fluid collection devices herein limit or eliminate sores and discomfort compared to conventional fluid collection devices.

Figure 1B:
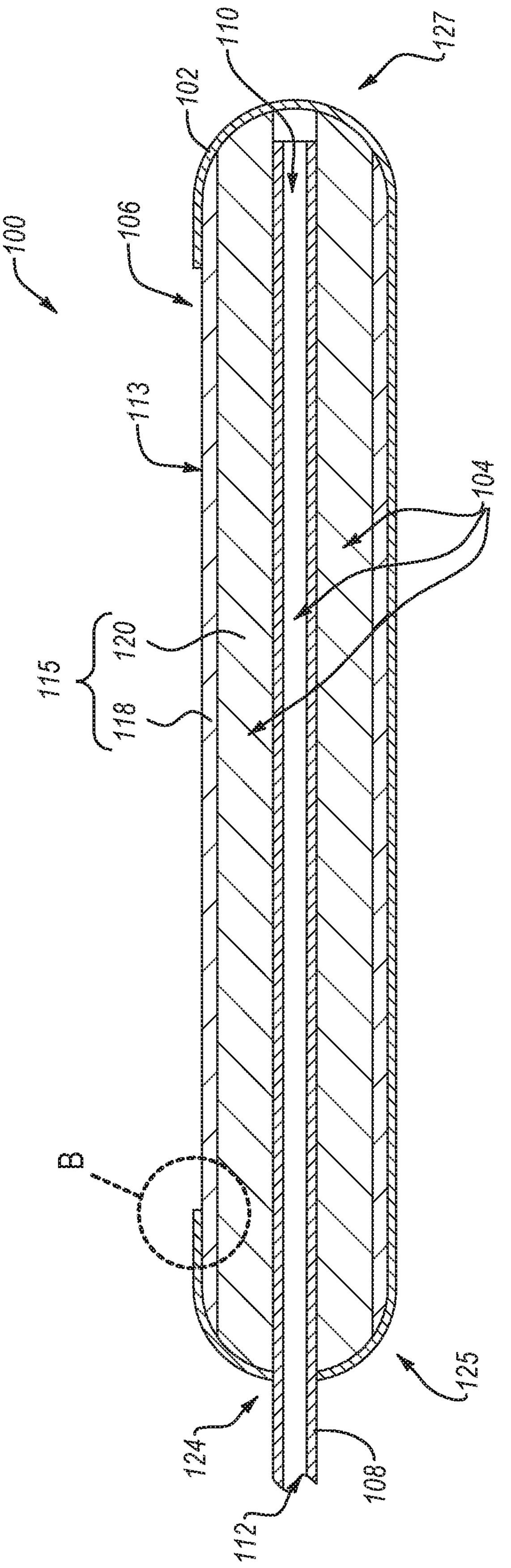
FIG. 1B is a cross-sectional view of the fluid collection device of FIG. 1A taken along the plane A-A, according to an embodiment.

FIG. 1A is an isometric view of a fluid collection device 100, according to an embodiment. FIG. 1B is a cross-sectional view of the fluid collection device of FIG. 1A taken along the plane A-A, according to an embodiment. References to both FIGS. 1A and 1B are made below. The fluid collection device 100 may include a fluid impermeable coating 102 and wicking material 115. The wicking material 115 may be disposed within the fluid impermeable coating 102. The fluid collection device 100 may also include a conduit 108. The conduit 108 may be at least partially disposed within wicking material 115.

The fluid impermeable coating 102 at least partially defines at least a portion of an outer surface of the fluid collection device 100. The fluid impermeable coating 102 at least partially defines a chamber 104 in the fluid collection device 100 (e.g., interior region of the fluid collection device 100) and an opening 106. The opening 106 is defined by, or formed in and extends through, the fluid impermeable coating 102 thereby enables fluids to enter the chamber 104 from outside of the fluid collection device 100. The chamber 104 contains at least a portion of the wicking material 115 and conduit 108. The wicking material 115 is exposed through the opening 106. The opening 106 may be located on a portion of the fluid collection device 100 expected to be positioned adjacent to a female urethra, such as on or between the labia majora of a female user. For example, the opening 106 may allow urine to pass to the wicking material 115 from a wearer and at least temporarily retain the fluid within the chamber 104.

The fluid impermeable coating 102 at least temporarily retains or stores fluids in the chamber 104. The fluid impermeable coating 102 may be formed of a material and/or have a thickness selected to provide a relatively soft feel of the fluid collection device 100 against the skin of a wearer. The fluid impermeable coating 102 may be a thin layer of material disposed on or in an outer surface 113 of the wicking material 115.

In some embodiments, the fluid impermeable coating 102 may be formed of a material with a relatively soft feel, such as with a hardness lower than an average silicone. The fluid impermeable coatings 102 disclosed herein prevent or limit discontinuities between an outer impermeable barrier or shell and the wicking material, such as when a conventional silicone outer shell is used. The relatively thin and/or soft material of the fluid impermeable coating 102 prevents discomfort from relatively stiff or hard materials traditionally used in fluid collection devices when positioned against a wearer, provides a substantially uniform feel over the entire device, and provides a relatively soft feel at an outer surface of the device compared to devices with molded fluid impermeable barriers.

The fluid impermeable coating 102 may be formed of any suitable fluid impermeable materials, such as a fluid impermeable polymer, wax, nanocellulose, nanoparticles, another suitable material, or combinations thereof. As such, the fluid impermeable coating 102 may prevent at least some of the fluid(s) from exiting the portions of the chamber 104 that are spaced from the opening 106. The fluid impermeable coating 102 may be a hydrophobic material. For example, the fluid impermeable coating may include one or more of silicone, polypropylene, polyethylene, polyethylene terephthalate, polystyrene, polyurethane, a polycarbonate, polychloroprene, vinyl, polyvinyl chloride, latex, silanes (e.g., an halogenated alkyl silane), perfluorinated polymers, etc. The fluid impermeable coating 102 may include a superhydrophobic material, such as fluorocarbon polymers, fluorosilane polymers, metal oxide polystyrene nanocomposites (e.g., $MnO_2$ or ZnO), textured silica, carbon nanotubes, etc. The fluid impermeable coating 102 may be an elastomeric material, such as silicone-rubber. Other suitable materials include thermoplastic elastomers such as one or more of thermoplastic styrene-containing block copolymers, thermoplastic polyurethanes, thermoplastic copolyesters, thermoplastic olefins, thermoplastic polyamides, or the like.

In some examples, the fluid impermeable coating 102 may be oleophobic. In some examples, the material of the fluid impermeable coating 102 may also be composed to reduce or prevent dissolution of the fluid impermeable coating 102 in the presence of acid or basic body fluids.

In some embodiments, the fluid impermeable coating 102 may be air permeable and fluid impermeable. In such an example, the fluid impermeable coating 102 may be formed of a hydrophobic material that defines a plurality of pores sized and shaped to allow gases to pass therethrough but retain liquids.

The thickness of the fluid impermeable coating 102 may be kept to a minimum, to provide a fluid impermeable barrier, to have a smooth discontinuity-free feel, and allow the fluid collection device to have the overall feel of the outermost portion of the wicking material 115. For example, the thickness of the fluid impermeable coating 102 may be sufficiently thin to provide a tactile feel of the outermost portion of the wicking material 115 (e.g., fluid permeable membrane 118). The thickness of the fluid impermeable coating 102 may be less than about 2 mm, about 10 μm to about 2 mm, about 500 μm to about 1.5 mm, about 100 μm to about 1 mm, about 1 mm to about 2 mm, about 10 μm to about 200 μm, about 10 μm to about 500 μm, about 200 μm to about 500 μm, more than about 500 μm, less than about 1 mm, less than about 500 μm, or less than about 100 μm.

In some examples, the fluid impermeable coating 102 may include multiple layers of any of the foregoing materials. For example, the fluid impermeable coating 102 may include a thin layer (e.g., less than 1 mm) of latex coated in textured silica, such as on the outer side of the latex layer or the inner, chamber-facing side of the latex layer.

In an example, at least one or more portions of an outer surface of the fluid impermeable coating 102 may be formed from a soft and/or smooth material thereby reducing discomfort, chafing, or sores on the skin of the user. For example, any of the materials disclosed herein for the fluid impermeable coating 102 may be provided with one or more portions having a relative smooth texture, such as having surface roughness measured in Ra value of less than about 30 micrometers (μm), such as 0.1 μm to 30 μm, 0.5 μm to about 20 μm, 1 μm to 10 μm, 0.1 μm to 5 μm, less than 20 μm, less than 15 μm, less than 10 μm, less than 5 μm, or less than 2 μm.

In some examples, the fluid impermeable coating 102 may be relatively soft such as having a relatively low hardness (e.g., a Shore A hardness value of less than 40, such as less than about 30, less than about 20, or less than about 10; and in some cases a Shore 00 hardness value of less than about 50 or less than about 40). By using a relatively soft material, such as any of those described herein, the fluid impermeable coating 102 may be more comfortable than fluid collection devices that use relatively harder materials such as an outer shell made from rubber or silicone having an average hardness (e.g., a Shore A hardness of 40 or more).

The fluid impermeable coating 102 may include markings thereon, such as one or more markings to aid a user in aligning the device 100 on the wearer. For example, a line on the fluid impermeable coating 102 (e.g., opposite the opening 106) may allow a healthcare professional to align the opening 106 over the urethra of the wearer. The markings may include one or more of alignment guide or an orientation indicator, such as a stripe or hashes. Such markings may be positioned to align the device 100 to one or more anatomical features such as a pubic bone, etc.

As shown in FIG. 1B, the fluid impermeable coating 102 may be disposed on an outermost portion of the wicking material 115. For example, the fluid impermeable coating 102 may be a layer of material adhered to an outer surface 113 of the wicking material 115.

The wicking material 115 may be disposed within the fluid impermeable coating 102. The wicking material 115 may include permeable material designed to wick or pass fluid therethrough. The permeable properties referred to herein may be wicking, capillary action, diffusion, or other similar properties or processes, and are referred to herein as "permeable" and/or "wicking." Such "wicking" may not include absorption into the wicking material. The wicking material 115 may collect the fluid that travels through the opening 106. The wicking material 115 may include more than one material, such as a plurality of materials. The plurality of materials may include a plurality of layers concentrically disposed within one another. The concentrically disposed layers of wicking materials may exhibit a gradient of wicking, such as where the innermost wicking material includes the greatest or least wicking ability of the plurality of materials. In some examples, the plurality of layers of wicking materials may be non-concentrically arranged, such as having an innermost layer of wicking material located off-center of one or more outer layers of wicking material(s) and/or fluid impermeable coating. In such examples, the conduit 108 may be non-concentrically located in the fluid collection device 100, such as in the non-concentrically located innermost layer of wicking material.

In some examples, the wicking material 115 may include one or more of a fluid permeable support 120 or a fluid permeable membrane 118. For example, the fluid collection device 100 may include a fluid permeable membrane 118 disposed in the chamber 104. The fluid permeable membrane 118 may cover at least a portion (e.g., all) of the opening 106. The fluid permeable membrane 118 may be configured to wick any fluid away from the opening 106 thereby preventing the fluid from escaping the chamber 104. The fluid permeable membrane 118 may also wick the fluid generally towards an interior of the chamber 104, as discussed in more detail below. The fluid permeable membrane 118 may include any material that may wick the fluid. For example, the fluid permeable membrane 118 may include fabric, such as a gauze (e.g., a silk, linen, polyester, Rayon, cotton, or blends of gauzes), another soft fabric, or another smooth fabric. The fluid permeable membrane 118 may include spun plastic fibers. In some examples, the fluid permeable membrane 118 may include an open cell foam, such as a polyester foam. Forming the fluid permeable membrane 118 from gauze, soft fabric, and/or smooth fabric may reduce chafing caused by the fluid collection device 100 rubbing against the skin of a user.

The fluid permeable support 120 is disposed in the chamber 104, such as concentrically within the fluid permeable membrane 118. The fluid permeable support 120 may support the fluid permeable membrane 118 due to the relatively malleable form of the fluid permeable membrane material 118. For example, the fluid permeable membrane 118 may be formed from a foldable, flimsy, or otherwise easily deformable material, such as a gauze type fabric composed to wick but not absorb fluids. Accordingly, the fluid permeable membrane may 118 be held in shape and place or otherwise be supported by the fluid permeable support 120. In some examples, the fluid permeable support 120 may be positioned such that the fluid permeable membrane 118 is disposed between the fluid permeable support and the fluid impermeable coating 102. As such, the fluid permeable support 120 may support and maintain the position of the fluid permeable membrane 118. The fluid permeable support 120 may include a relatively more rigid or dense material than the fluid permeable membrane 118. The fluid permeable support 120 may be formed from any fluid permeable material that is less deformable than the fluid permeable membrane 118, such as any of the materials disclosed herein for the fluid impermeable membrane 118, in a more dense or rigid form. For example, the fluid permeable support 120 may include a porous polymer (e.g., nylon, polyester, polyurethane, polyethylene, polypropylene, etc.) structure or an open cell foam. The fluid permeable support 120 may include spun plastic fibers. In some examples, the fluid permeable support 120 may be formed from a natural material, such as cotton, wool, silk, or combinations thereof. In some examples, the fluid permeable support 120 may be formed from fabric, felt, gauze, or combinations thereof. The fluid permeable support 120 may be resiliently flexible to help impart resiliency and flexibility to the fluid collection device 100. In some examples, the fluid permeable support 120 may be omitted from the fluid collection device 100. For example, the wicking material 115 may include only the fluid permeable membrane 118. In some examples, the fluid permeable membrane 118 may be optional. For example, the wicking material 115 may include only the fluid permeable support 120. The fluid permeable support 120 may have a greater density than the fluid permeable membrane 118 or be may be made from a more rigid material than the fluid permeable membrane 118.

The wicking material 115 (e.g., at least the fluid permeable support) may provide the structural support to maintain a general shape of the fluid collection device 100, which may be resiliently flexible. For example, the wicking material 115 may be in a substantially cylindrical shape, a substantially flat shape, a substantially prismatic shape, etc. Likewise, the materials applied thereover (e.g., the fluid impermeable coating 102) may exhibit the same shape.

The fluid impermeable coating 102 and the wicking material 115 may be configured to receive the conduit 108 at least partially within the chamber 104. For example, at least one of the fluid permeable membrane 118 and the fluid permeable support 120 may be configured to form a space that accommodates the conduit 108. In another example, the fluid impermeable coating 102 may define an aperture sized to receive the conduit 108 (e.g., at least one tube). The at least one conduit 108 may be disposed in the chamber 104 via the aperture 124, such as via an aperture formed in the first end region 132 of the fluid collection device. The aperture 124 may be sized and shaped to form an at least substantially fluid tight seal against the conduit 108 thereby substantially preventing the fluids from escaping the chamber 104. In some examples (not shown), the aperture 124 may be disposed on the second end region 134. In such examples, the conduit 108 may be disposed in only the second end region 134 with the inlet 110 being disposed in the second end region 134 (e.g., the reservoir 122, FIG. 2B).

Locating the inlet 110 in a position of the fluid collection device that is intended to be positioned at or near a gravimetrically low point of the chamber 104 when the fluid collection device is in use enables the conduit 108 to receive more of the fluids than if inlet 110 was located elsewhere and reduces the likelihood of pooling (e.g., pooling of the fluids may cause microbe growth and foul odors). For instance, the fluids in the wicking material 115 may flow in any direction due to capillary forces. However, the fluids may exhibit a preference to flow in the direction of gravity, especially when at least a portion of the wicking material 115 is saturated with the fluids.

As discussed in more detail below, the conduit 108 is sized and shaped to be coupled to, and at least partially extend between, one or more of a fluid storage container (not shown) and a vacuum source (not shown). In an example, the conduit 108 is configured to be directly connected to the vacuum source. In such an example, the conduit 108 may extend from the fluid impermeable coating 102 by at least one foot, at least two feet, at least three feet, or at least six feet. In another example, the conduit 108 is configured to be indirectly connected to at least one of the fluid storage container and the vacuum source. In some examples, the conduit 108 may be secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The term "coating" is not intended to be limited to only material disposed on an outer surface of another material, rather a coating may be an entire layer, a portion of layer, or a separate layer disposed on or in the wicking material as disclosed in more detail herein.

Figure 1C:
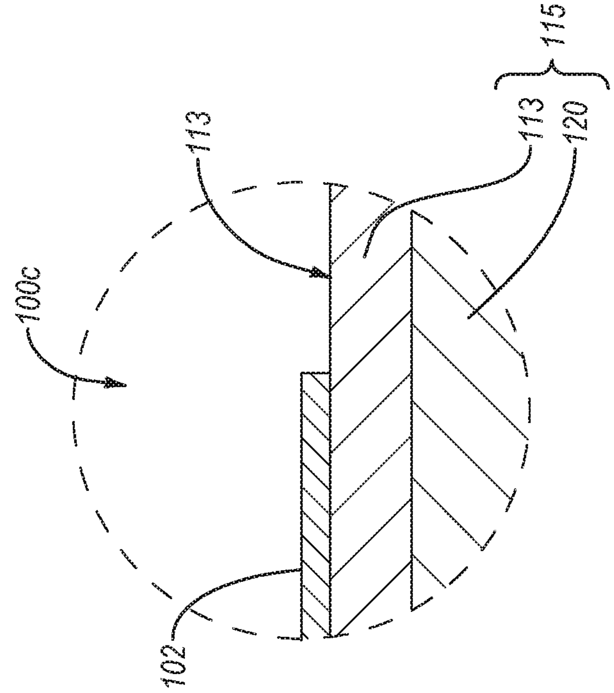
FIGS. 1C and 1D are cross-sectional views of the area B of FIG. 1B, according to various embodiments.
Figure 1D:
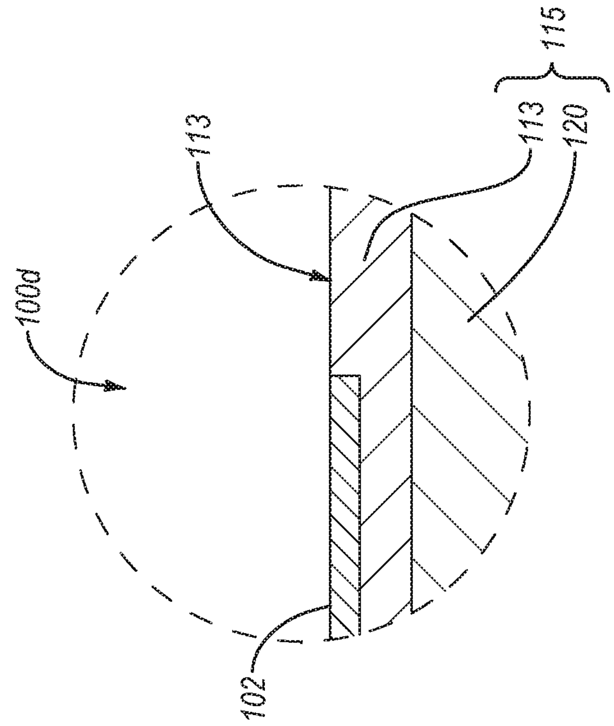

As shown in FIGS. 1C and 1D, the fluid impermeable coating 102 may be disposed on or in the wicking material 115. FIGS. 1C and 1D are cross-sectional views of the area B of FIG. 1B. As shown in FIG. 1C, the fluid collection device 100*c* includes the fluid impermeable coating 102 disposed on the outer surface 113 of the wicking material 115 (e.g., the fluid permeable membrane 118). The fluid collection device 100*c* is similar or identical to the fluid collection device 100 in one or more aspects. The fluid impermeable coating 102 is deposited on the surface 113 of the wicking material 115. The fluid impermeable coating 102 may be cast, coated, wrapped, sprayed, or otherwise deposited on the surface 113 to a selected thickness, such as any of the thicknesses disclosed herein. In some examples, the fluid impermeable coating may be adhered to the outermost portion of the wicking material (e.g., fluid impermeable membrane), such as with an adhesive or may be interfacially self-bonded to the wicking material such as via dip coating.

In some embodiments, the fluid impermeable coating 102 may be least partially embedded or otherwise disposed in the outermost portion of the wicking material 115. As shown in FIG. 1D, the fluid collection device 100*d* includes the fluid impermeable coating 102 embedded in the outer surface 113 of the wicking material 115 (e.g., the fluid permeable membrane 118). The fluid collection device 100*d* is similar or identical to the fluid collection device 100 in one or more aspects. The fluid impermeable coating 102 is deposited in the outer most portion of the wicking material 115 and at least partially defines the surface 113 of the wicking material 115. In such examples, the outer surface of the fluid impermeable coating 102 may be coextensive with the outer surface 113 of the wicking material 115 as shown. In some examples (not shown), the outer surface of the fluid impermeable coating 102 may extend from within the wicking material 115 to beyond with the outer surface 113 of the wicking material 115. The fluid impermeable coating 102 may be cast, coated, sprayed, permeated, or otherwise incorporated into the wicking material 115 at the surface 113 to a selected depth therein (e.g., coating thickness), such as to any of the thicknesses disclosed herein. Upon application, the wicking material 115 may at least partially wick the fluid impermeable membrane material into the outer surface thereof. In such examples, the fluid impermeable coating material may be infiltrated into the wicking material 115 sufficient to cause the infiltrated portion of the wicking material to be fluid impermeable.

As shown in FIG. 1B, the wicking material 115 (e.g., one or more of the fluid permeable membrane 118 or the fluid permeable support 120) may at least substantially completely fill portions of the chamber 104 that are not occupied by the conduit 108. For example, the wicking material 115 may fill the portions of the chamber 104 that are not occupied by the conduit 108 when the fluid impermeable coating 102 is disposed over the entire outer surface of the wicking material 115 (except for the opening 106).

In some examples (FIGS. 2A-3B), the fluid permeable membrane 118 and the fluid permeable support may not substantially completely fill the portions of the chamber 104 that are not occupied by the conduit 108. In such examples, the fluid collection device 100 may include the reservoir (e.g., void space) disposed in the chamber 104. The reservoir may be a void space defined between the wicking material in the chamber 104 and the interior surface of the fluid impermeable coating 102 or an end cap (FIGS. 2A-3B). At least some of the fluid wicked by the wicking material 115 may drain out of the wicking material 115 and collect in the reservoir.

Returning to FIGS. 1A and 1B, the conduit 108 may be disposed within the wicking material 115 and includes the inlet 110 positioned within the fluid collection device 100 and the outlet for fluidly coupling (e.g., plumbed or otherwise fluidly connected) to a vacuum source. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In examples, the conduit 108 may include silicon or latex. The conduit 108 includes an inlet 110 at the second end region 134 and an outlet 112 at a first end region 132 positioned downstream from the inlet 110. The inlet 110 of the conduit 108 fluidly couples the chamber 104 with a fluid storage container or a vacuum source for removing fluids from the fluid collection device 100. The fluid may be removed from the chamber 104 via the conduit 108. As suction or vacuum force is applied or formed in the conduit 108 by the vacuum source (FIG. 4), the fluid in the chamber 104 may be drawn into the inlet 110 and out of the fluid collection device 100 via the conduit 108.

In some examples, the inlet 110 may be disposed in an innermost or gravimetrically low spot in the chamber 104. For example, the conduit 108 may extend far enough into the chamber 104 to position the inlet 110 in a gravimetrically low point of the chamber 104 such as in a fluid reservoir within the chamber 104 the fluid collection device 100.

The fluid collection device 100 and components thereof may be deformable (e.g., bendable) responsive to pressure applied thereto. For example, the fluid collection device 100 and the components thereof may bend to conform to the anatomical contours of the user, such as when disposed between a garment and the user. In examples, the fluid collection device 100 may bend when disposing proximate to the urethra (e.g., between the labia) when the fluid collection device 100 is positioned on a wearer (e.g., user).

The fluid collection device 100 is an example of a female fluid collection device 100 sized, shaped, and otherwise configured to receive fluids from a female user. For example, the fluid collection device 100 or at least one of the components therein may be substantially cylindrical, ellipsoid, prismatic, or any other shape suitable for complementing or contouring to the vaginal region of a female subject. The opening 106 may be configured to be positioned adjacent to a female urethra. The opening 106 may be positioned on an upward or inward (e.g., toward a user) facing portion of the fluid collection device 100.

In the illustrated example, the conduit 108 is at least partially disposed in the chamber 104. For example, the conduit 108 may extend into the fluid impermeable coating 102 from the first end region 125 and may extend to the second end region 127 to a point proximate to end of the fluid collection device 100 (portion of the device configured to be disposed at a gravimetrically low point of the device when in use). As shown in FIG. 1B, the end of inlet 110 may be offset from the fluid impermeable coating 102 to allow fluid to be drawn therethrough. In some examples, the conduit 108 may be perforated, such as at the inlet end to allow radial collection of fluids from the wicking material. In some examples (not shown), the conduit 108 may enter the second end region 127 and the inlet 110 of the conduit 108 may be disposed in the second end region 127. The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as to by having one or more of a diameter or wall thickness that allows the conduit to be flexible.

The fluid collection device 100 may be positioned proximate to the female urethra (e.g. on or between the labia) and urine may enter the chamber 104 of the fluid collection device 100 via the opening 106. The fluid collection device 100 receives the fluids into the chamber 104 via the opening 106. For example, the opening 106 may exhibit an elongated shape that is sized and positioned to extend from a first location below the urethral opening (e.g., at or near the anus or the vaginal opening) to a second location above the urethral opening (e.g., at or near the clitoris or the mons pubis). The opening 106 may exhibit an elongated shape since the space between the legs of a female is relatively small when the legs of the female of closed thereby only permitting the flow of the fluids along a path that corresponds to the elongated shape of the opening 106. The opening 106 in the fluid impermeable coating 102 may exhibit a width that is measured transverse to the longitudinal direction of the fluid collection device 100 and may be at least about 10% of the circumference of the fluid collection device 100, such as about 25%, 30%, 40%, 50%, 60%, 75%, 85%, 100% or ranges between any combination of the foregoing, of the circumference of the fluid collection device 100. The opening 106 may exhibit a width that is greater than 50% of the circumference of the fluid collection device 100 since the vacuum (e.g., suction) pulls the fluid into the conduit 108.

In an example, one or more portions of the fluid impermeable coating 102 may be configured to be attached to a patient or a garment worn by a user, such as adhesively attached (e.g., with a hydrogel adhesive, such as a hydrogel layer as disclosed in U.S. Pat. No. 10,226,376, the disclosure of which is incorporated herein by this reference in its entirety). In some examples, the opening 106 may be longitudinally oriented (e.g., having a major axis parallel to the longitudinal axis of the device 100). In some examples, (not shown) the opening 106 may be laterally oriented (e.g., having a major axis perpendicular to the longitudinal axis of the device 100).

In an example, the conduit 108 is configured to be at least insertable into the chamber 104. In such an example, the conduit 108 may include one or more markers (not shown) on an exterior thereof that are configured to facilitate insertion of the conduit 108 into the chamber 104. For example, the conduit 108 may include one or more markings thereon that are configured to prevent over or under insertion of the conduit 108, such as when the conduit 108 defines an inlet 110 configured to be disposed in or adjacent to a reservoir in the fluid collection device (FIGS. 2B and 2C). In another example, the conduit 108 may include one or more markings thereon that are configured to facilitate correct rotation or depth of insertion of the conduit 108 in the chamber 104. In an example, the one or more markings may include a line, a dot, a sticker, or any other suitable marking. In some examples, the conduit may be frosted or opaque (e.g., black) to obscure visibility of the fluids therein.

Other examples of fluid impermeable materials, fluid permeable membranes, fluid permeable supports, chambers, and their shapes and configurations, which may be utilized in the examples described herein, are disclosed in U.S. patent Ser. No. 16/369,676 filed on Mar. 29, 2019 and U.S. patent application Ser. No. 15/260,103 filed on Sep. 8, 2016 (published as US 2016-0374848 on Dec. 29, 2016), the disclosure of each of which is incorporated herein, in its entirety, by this reference.

In some examples, the fluid collection device 100 may include a reservoir therein. In such examples, the fluid collection device may include one or more end caps configured to retain the first end region and the second end region of the wicking material therein.

Figure 2A:
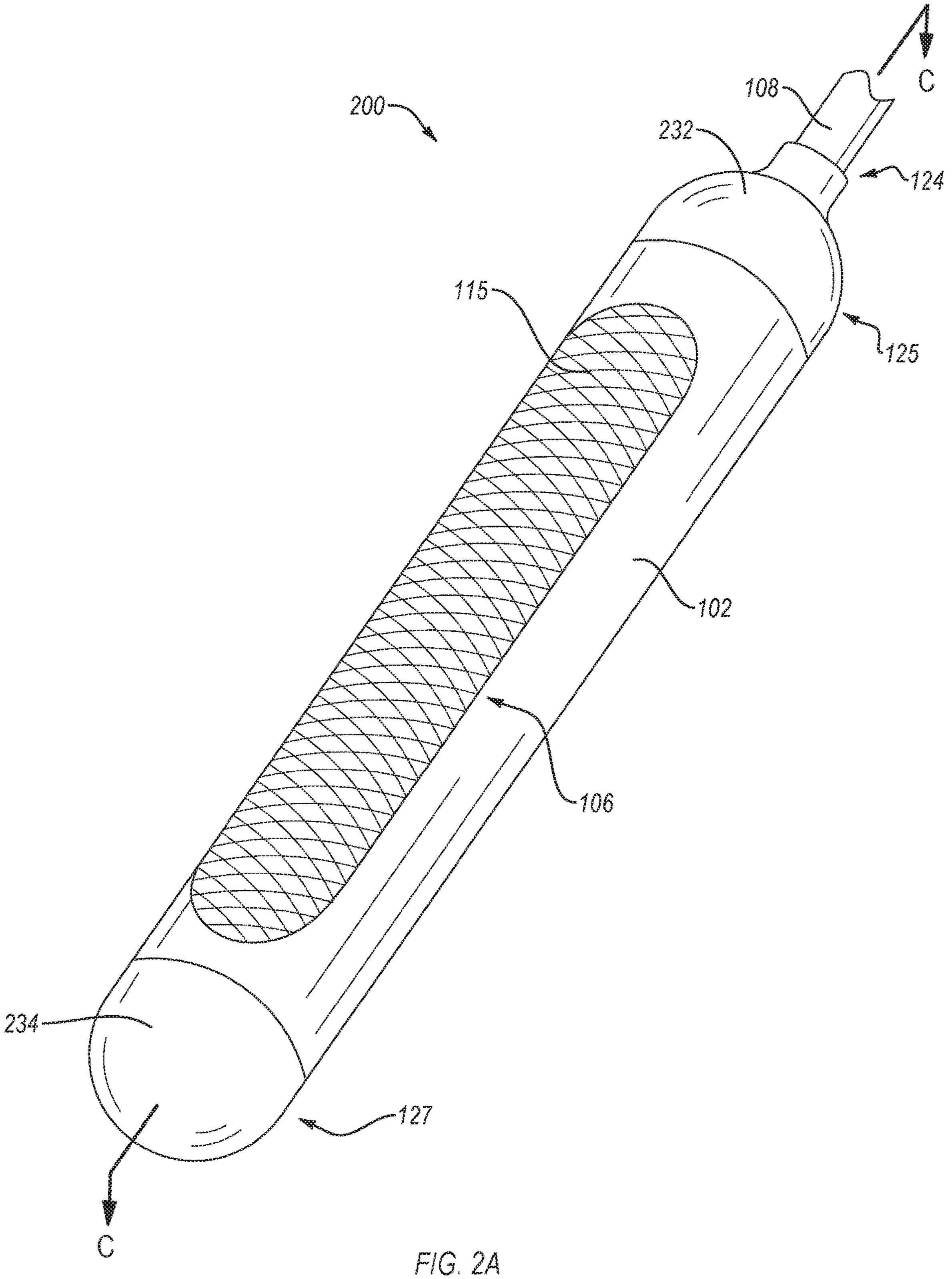
FIG. 2A is an isometric view of a fluid collection device, according to an embodiment.
Figure 2B:
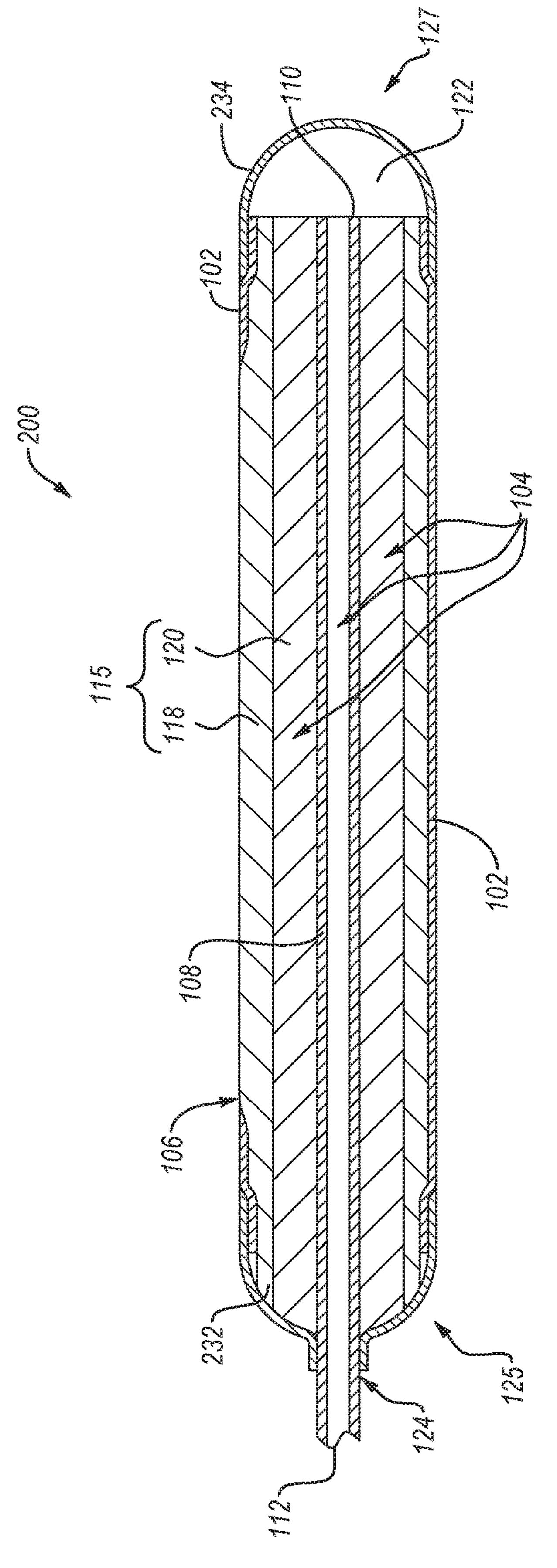
FIGS. 2B and 2C are cross-sectional views of the fluid collection device of FIG. 2A taken along the plane C-C, according to various embodiments.
Figure 2C:
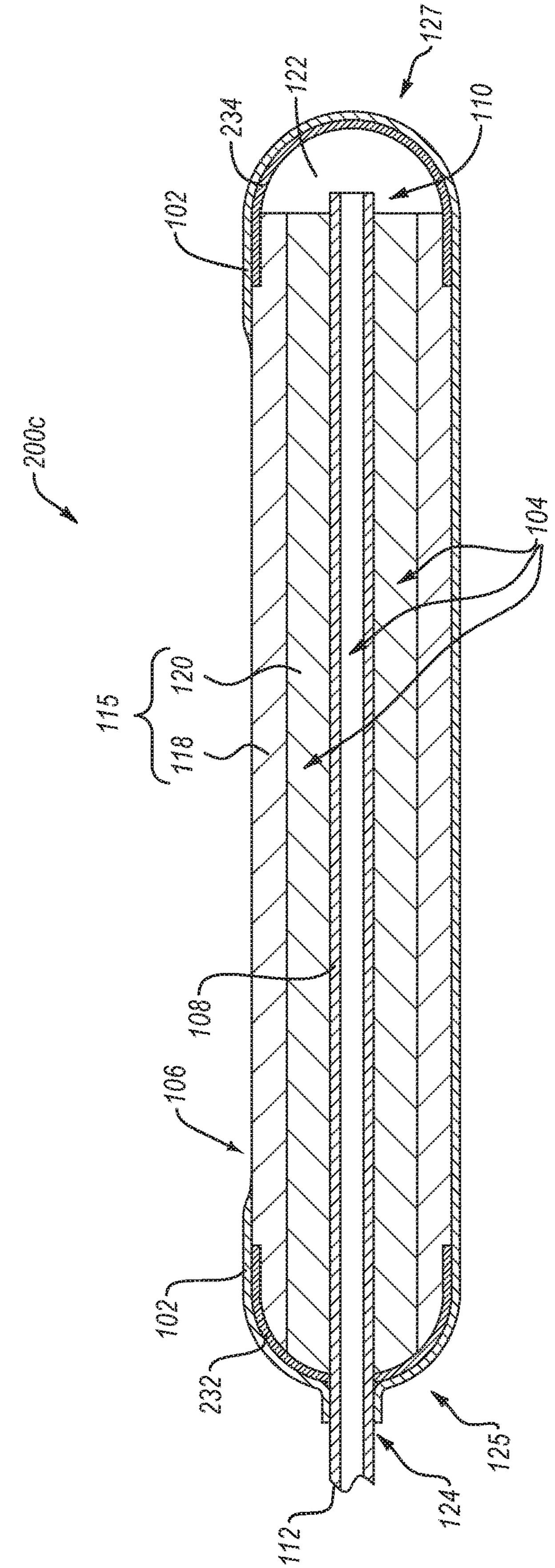

FIG. 2A is an isometric view of a fluid collection device 200, according to an embodiment. FIG. 2B is a cross-sectional view of the fluid collection device of FIG. 2A taken along the plane C-C, according to an embodiment. FIGS. 2A and 2B are described in detail below. The fluid collection device 200 may be similar or identical to the fluid collection device 100 in one or more aspects. For example, the fluid collection device 200 includes a fluid impermeable coating 102, wicking material 115, and conduit 108 as disclosed herein. The fluid collection device 200 includes at least one endcap, such as the first endcap 232 and the second endcap 234. The wicking material 115 may be disposed within the fluid impermeable coating 102. The at least one endcap may be disposed over the fluid impermeable coating 102 and the wicking material 115 at the first end region 125 and the second end region 127. Collectively, the fluid impermeable coating 102 and the at least one endcap define the chamber 104. The fluid collection device 200 may include a reservoir 122 within the chamber 104, such as a void space defined between the second endcap 234 and the wicking material 115. The fluid collection device 200 may also include the conduit 108. The conduit 108 may be at least partially disposed within wicking material 115 as disclosed herein.

As shown, the fluid impermeable coating 102 may be disposed over the wicking material 115 and the endcaps 232 and 234 may be disposed over the end regions of the coated wicking material. The endcaps may be sealed to the fluid impermeable coating, such as via a tension fit or a fluid impermeable adhesive. The first and second endcaps 232 and 234 may have a selected cross-sectional shape (e.g., when viewed along the longitudinal axis), such as circular, elliptical, triangular, rectangular, or the like. The endcaps 232 and 234 may retain the wicking material 115 in the selected cross-sectional shape. For example, the first and second endcaps 232 and 234 may retain the wicking material 115 in a substantially cylindrical configuration as shown.

The first endcap 232 may be disposed over the wicking material 115 and fluid impermeable coating 102 at the first end region 125 of the fluid collection device 200. The first endcap 232 may include the aperture 124 sized and shaped to accept and seal against the conduit 108 passed therethrough.

The second endcap 234 may be disposed over the wicking material 115 and fluid impermeable coating 102 at the second end region 127. The second endcap 234 at least partially defines the reservoir 122 to collect fluid therein. The fluid impermeable coating 102 may also at least partially define the reservoir 122.

The at least one endcap may be formed of a fluid impermeable material. For example, the endcaps 232 and 234 may be made of the same or similar materials as the fluid impermeable coating 102. The at least one endcap (e.g., second endcap 234) may include a more rigid material than the fluid impermeable coating 102, such as to allow the reservoir 122 to maintain a substantially constant volume when in use. The at least one endcap may be made of a resilient material to retain or return to a selected shape if deformed via external pressure.

The reservoir 122 may be located at the portion of the chamber 104 that is closest to the inlet 110 (e.g., the second end region), such as under the second endcap 234. However, the reservoir 122 may be located at different locations in the chamber 104. For example, the reservoir 122 may be located at the end of the chamber 104 that is closest to the outlet 112, such as under the first endcap 232. In another example, fluid collection device 100 may include multiple reservoirs, such as a first reservoir that is located at the second end region 127 and a second reservoir that is located at the first end region 125. In another example, the fluid permeable support 120 is spaced from at least a portion of the conduit 108, and the reservoir 122 may be the space between the fluid permeable support 120 and the conduit 108.

As shown in FIG. 2B, the inlet 110 of the conduit 108 may be coextensive with the end of the wicking material 115 at the second end region of the fluid collection device 200. In some examples, the inlet 110 of the conduit 108 may extend beyond the end of the wicking material 115 at the second end region of the fluid collection device 200. In some examples, the inlet 110 of the conduit 108 may be disposed within the wicking material 115 such as recessed inside of the channel in the wicking material 115 at the second end region of the fluid collection device 200.

In some examples, the one or more of the wicking material 115 and the fluid impermeable coating 102 at the first and/or second end regions of the fluid collection device 200 may have a stepped configuration selected to provide a substantially constant dimension (e.g., diameter) at the outer surface of the fluid collection device. Such a stepped configuration may include progressively smaller diameters at the second end region 127 of the wicking material 115 to accommodate the thickness of the fluid impermeable coating 102 and/or second endcap 234. Accordingly, the fluid collection device 200 may have a substantially smooth outer surface, free of cusps, gaps, or other discontinuities.

In some embodiments, the fluid impermeable coating 102 may be disposed over the wicking material 115 and the at least one endcap.

FIG. 2C is a side cross-sectional view of the fluid collection device of FIG. 2A taken along the plane C-C, according to an embodiment. FIG. 2C depicts the fluid collection device 200*c*. The fluid collection device 200*c* may be similar or identical to the fluid collection device 100 or 200 in one or more aspects. For example, the fluid collection device 200*c* includes one or more of the wicking material 115, the at least one endcap, wicking material 115, and the conduit 108 disposed within the fluid impermeable coating 102. As shown, the fluid impermeable coating 102 may be disposed over the wicking material 115 and the endcaps 232 and 234, collectively, such as via spray application, dip coating, direct application, etc. The endcaps 232 and 234 may be sealed in the fluid impermeable coating along with the wicking material 115. The endcaps and/or the fluid impermeable coating 102 thereover may aid in retaining the shape of the wicking material 115. In some examples, the fluid impermeable coating 102 may be disposed on a portion of the wicking material 115 (e.g., to form the opening 106), the first endcap 232, and the second endcap 234. For example, the opening 106 may be formed by masking a portion of the wicking material 115 with a masking agent and dip coating the wicking material and first and second endcaps 232 and 234 in the fluid impermeable coating material. The masking agent may be removed from the wicking material to reveal the opening 106.

The first endcap 232 may be disposed over the wicking material 115 and within the fluid impermeable coating 102 at the first end region 125 of the fluid collection device 200*c*. The at least one endcap may be formed of a fluid impermeable material as disclosed above. The first endcap 232 may include the aperture 124 sized and shaped to accept and seal against the conduit 108 passed therethrough.

The second endcap 234 may be disposed over the wicking material 115 and within the fluid impermeable coating 102 at the second end region 127. The second endcap 234 at least partially defines the reservoir 122 to collect fluid therein. In such examples, the reservoir 122 may be a void space defined between the second endcap 234 and the wicking material 115.

As shown in FIG. 2C, in some embodiments, the inlet 110 of the conduit 108 may extend past the end of the wicking material 115 at the second end region of the fluid collection device 200*c*. In some embodiments, the inlet 110 of the conduit 108 may be coextensive with the end of the wicking material 115 or may be recessed inside of the channel in the wicking material 115 at the second end region 127.

In some examples, wicking material 115 may have a stepped configuration selected to accommodate the thickness of one or more of the at least one endcap and the fluid impermeable coating 102 to provide a substantially smooth outer surface for the fluid collection device when the fluid impermeable coating is applied thereover. Such a stepped configuration may include progressively smaller diameters at one or more of the first and second end regions 125 and 127 of the wicking material 115 to accommodate the first and second endcap 232 and 234. Accordingly, the fluid collection device 200 may have a substantially smooth outer surface free of cusps, gaps, steps, or other discontinuities. By coating the wicking material 115 and the at least one endcap in the fluid impermeable coating 102, the fluid collection device 200*c* may be less prone to leakage than the fluid collection device 200 which includes transitions between materials at the outer surface.

While the fluid collection devices for use by females are disclosed with respect to FIGS. 1A-2C, in some embodiments, fluid collection devices sized and shaped to be used by a male are also disclosed.

Figure 3A:
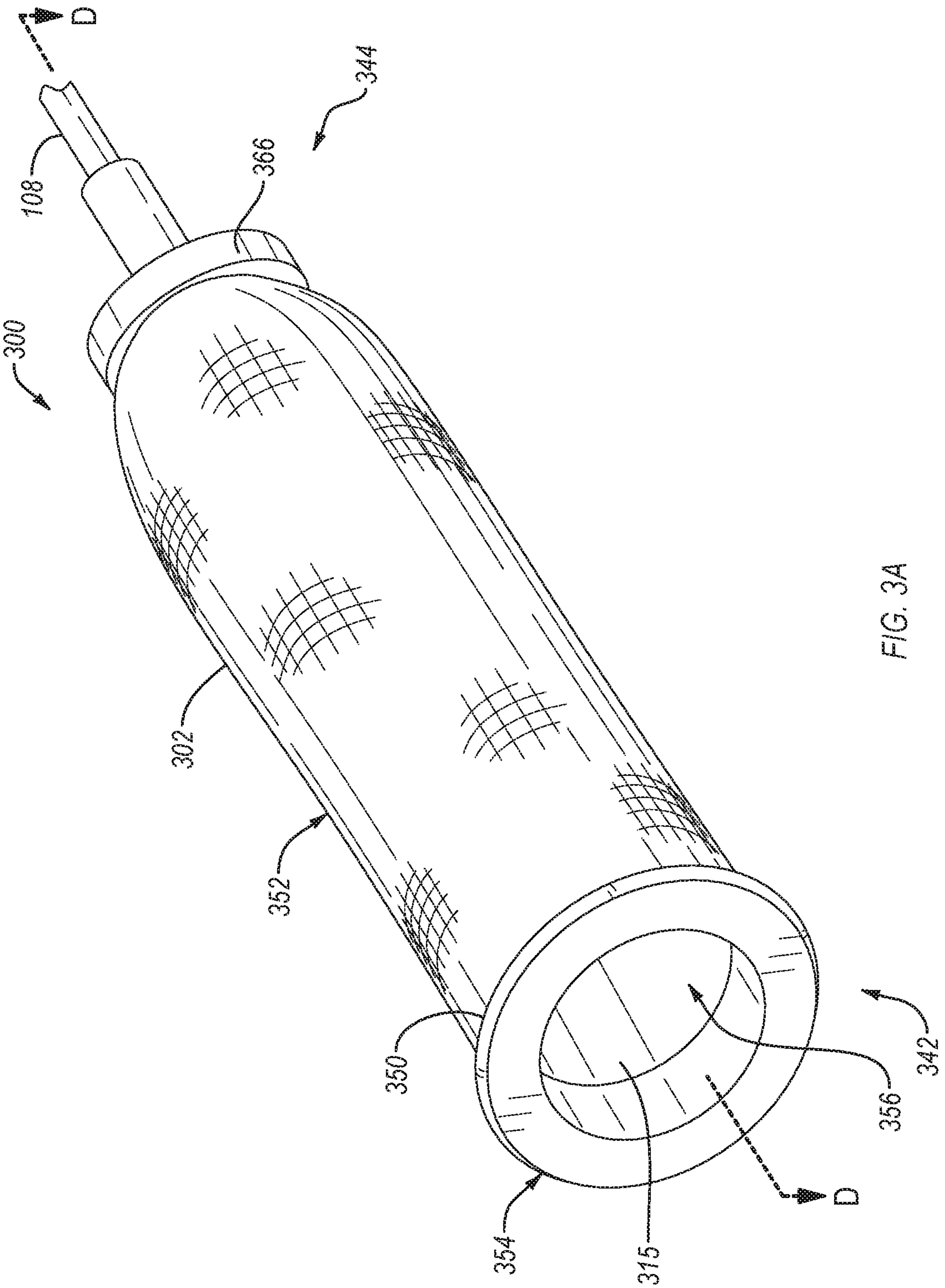
FIG. 3A is an isometric view of a fluid collection device, according to an embodiment.
Figure 3B:
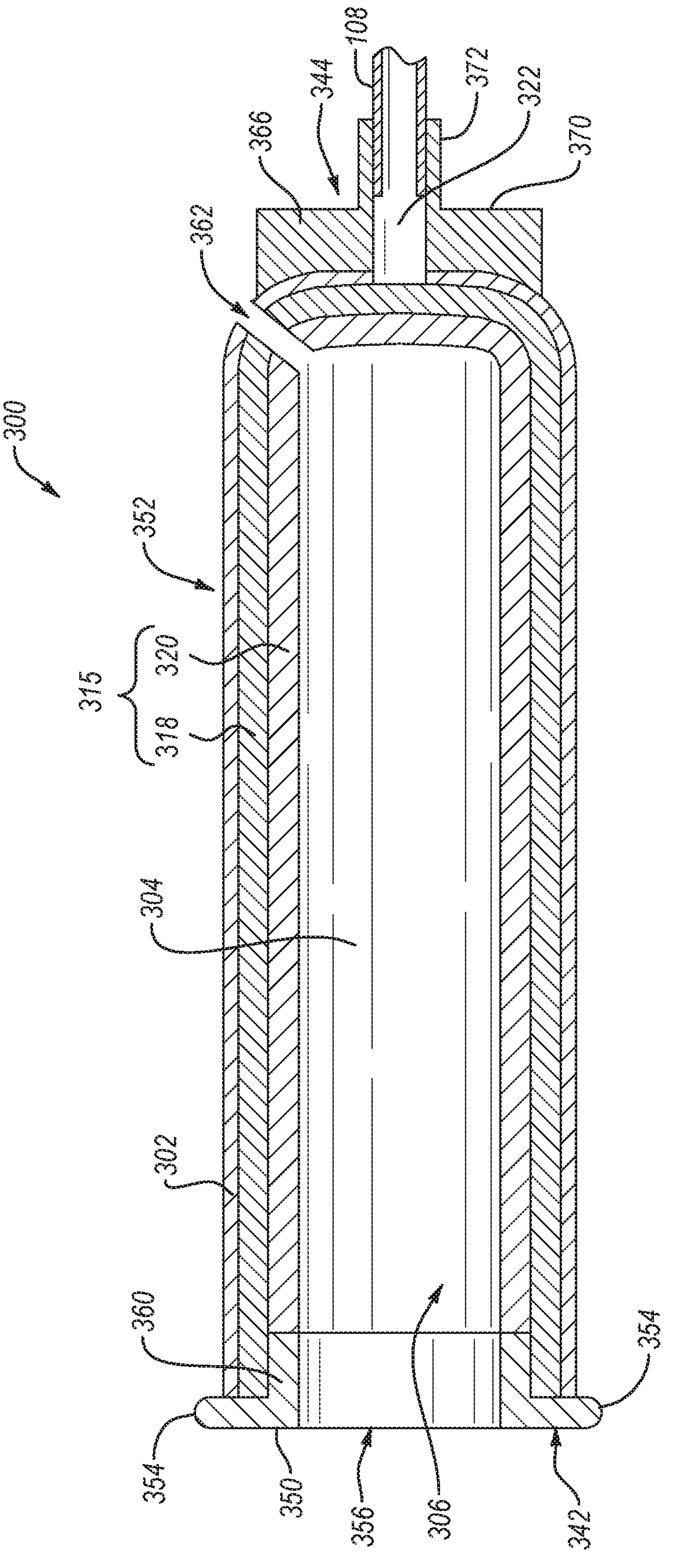
FIG. 3B is a cross-sectional view of a fluid collection device of FIG. 3A taken along the plane D-D, according an embodiment.

FIG. 3A is an isometric view of a fluid collection device 300, according to an embodiment. FIG. 3B is a cross-sectional view of a fluid collection device 300 of FIG. 3A, according at least some embodiments. Referring to FIGS. 3A and 3B, the fluid collection device 300 includes a receptacle 350 and a sheath 352 (e.g., cup shaped container). The receptacle 350 is sized, shaped, and made of a material to be disposed on the skin that surrounds the male urethra and have the male urethra positioned therethrough. For example, the receptacle 350 may include an annular base 354 that defines an opening 356 in the receptacle 350. The annular base 354 is sized and shaped to be positioned around the male urethra (e.g., positioned around the penis) and the opening 356 may be configured to have the male urethra positioned therethrough. The annular base 354 may also be sized, shaped, made of a material, or otherwise configured to be coupled (e.g., adhesively attached, such as with a hydrogel adhesive) to or disposed in a garment around the male urethra (e.g., around the penis). The receptacle 350 may be formed of any of the materials disclosed herein for the fluid impermeable coating 102, such as a silicone polymer. In an example, the annular base 354 may exhibit the general shape of the skin surface that the annular base 354 is selected to be coupled with and/or may be flexible thereby allowing the annular base 354 to conform to any shape of the skin surface.

The receptacle 350 also defines a hollowed region that is configured to receive (e.g., seal against) the sheath 352. For example, the receptacle 350 may include a flange 360 that extends longitudinally from the annular base 354. The flange 360 may be tall enough to prevent the sheath 352 from being accidentally removed from the receptacle 350 (e.g., at least 0.5 cm tall, 1 cm tall, at least 2 cm tall, or at least 5 cm tall). While depicted as being disposed within the sheath 352, in some examples the flange 360 may be disposed on the outer surface of the sheath 352.

The sheath 352 includes (e.g., may be formed from) a fluid impermeable coating 302 that is sized and shaped to fit into or around opening 356 (e.g., the hollowed region) and/or flange 360 of the receptacle 350. The fluid impermeable coating 302 may be disposed on wicking material 315. The sheath 352 may be shaped to contain, and allow for, different sizes and states of male penises. For example, the sheath 352 may be generally cup-shaped or tubular with a substantially closed end. In some examples, the sheath 352 may be substantially cylindrical with a closed distal end. The cylindrical sheath 352 may be "substantially" cylindrical in that the cylinder may be deformable and at least partially collapsible/expandable based on the size and state of the penis of the wearer. Accordingly, the penis of a wearer may be inserted into and contained within the sheath 352 whether in a flaccid or erect state.

The fluid impermeable coating 302 may be similar or identical to the fluid impermeable coating 102, in one or more aspects. The fluid impermeable coating 302 at least partially defines a chamber 304 therein. The fluid impermeable coating 302 may also define an opening 306 extending through the fluid impermeable coating 302 that is configured to have a male urethra positioned therethrough. The fluid impermeable coating 302 may also include at least one aperture 362 that allows the chamber 304 to remain substantially at atmospheric pressure. The aperture 362 may be disposed on any portion of the sheath 352, such as a portion not intended to serve as a reservoir for collected fluids. In some examples (not shown), the aperture 362 may extend through the cap 366 or be disposed beneath the cap 366. In some examples, the fluid collection device 300 may not include the aperture 362, such as when a more complete seal as desired for the chamber 304.

The fluid impermeable coating 302 may be disposed on, or at least partially infiltrated in, an outer surface of the wicking material 315 to form a fluid impermeable barrier separating the interior (e.g., chamber 304) of the fluid collection device 300 from the external environment. The wicking material 315 may be similar or identical to the wicking material 115 disclosed herein, in one or more aspects. For example, the wicking material 315 includes one or more of the fluid permeable membrane 118 or the fluid permeable support 120 disclosed herein. In some examples, the fluid permeable membrane 118 or the fluid permeable support 120 may be omitted from the wicking material 315. The fluid impermeable coating 302 may be adhered to the outer surface of the wicking material 315 (e.g., the fluid permeable membrane 118 or the fluid permeable support 120). Put another way, the fluid permeable support 120 may be disposed on an interior surface of the fluid impermeable coating 302. The fluid permeable membrane 118 may be disposed on an interior surface of the fluid permeable support 120, such as disposed concentrically within the fluid permeable support 120. In such examples, the fluid permeable membrane 118 may contact the skin of the wearer (e.g., penis) when in use. In some examples (not shown), the fluid permeable membrane 118 may be disposed at the outer surface of the wicking material 315, wherein the fluid impermeable coating 302 is adhered to the outer surface of the fluid permeable membrane 118. One or more of the fluid permeable membrane 118 or the fluid permeable support 120 may extend around at least a portion of the inner surface of the fluid impermeable coating 302.

To facilitate fluid collection and provide comfort, the sheath 352 may be flexible, relatively soft, and have a relatively smooth outer surface, thereby allowing the sheath 352 to correspond to the shape of a penis. For example, the sheath 352 may at least partially collapse when the penis is flaccid and at least partially expand and bend to the shape of the penis as the penis becomes erect.

The receptacle 350 may be more rigid than the sheath 352. For example, the receptacle 350 may be formed from a flexible polymer that is at least one of thicker than the entire sheath 352 or exhibits a Young's modulus that is greater than sheath 352. As such, the receptacle 350 may provide some structural support at or near the proximal end 342 of the fluid collection device 300. The higher rigidity of the receptacle 350 may cause the receptacle 350 to remain open, thereby facilitating insertion of the urethra (e.g., penis) into the fluid collection device 300. The relatively rigidity of the receptacle 350 enables the receptacle 350 to act as an attachment point to a wearer, wicking material 315, and/or the fluid impermeable coating 302. In some examples, the receptacle 350 may define a recess, include threads, or include any other attachment substrate for attaching the components of the fluid collection device 300, such as the wicking material 315 or the coating 302.

In some examples, the fluid collection device 300 includes a cap 366 at a distal end region 344. The cap 366 defines an interior channel through which the fluids may be removed from the fluid collection device 300. The interior channel is in fluid communication with the chamber 304. The cap 366 may be disposed over at least a portion of the distal end region 344 of one or more of the fluid impermeable coating 302 or the wicking material 315. The cap 366 may be made of a polymer, rubber, or other fluid impermeable material. The cap 366 may be attached to one or more of the fluid impermeable coating 302, the wicking material 315, or the conduit 108. The cap 366 may have a laterally extending flange 370 and a longitudinally extending flange 372. The laterally extending flange 370 may cover at least a portion of the distal end region 344 of the fluid collection device 300. The longitudinally extending flange 372 may extend a distance from the wicking material 315. The longitudinally extending flange 372 is sized and configured to receive and fluidly seal against the conduit 108, such as within the interior channel. The conduit 108 may extend a distance within the cap 366, such as to the wicking material 315, through the wicking material 315, or to a point set-off from the wicking material 315. In the latter example, as depicted in FIG. 3B, the interior channel of the cap 366 may define a reservoir 322 therein. The reservoir 322 is an unoccupied portion of the cap 366 and is void of other material. In some examples, the reservoir 322 is defined at least partially by the wicking material 315 and the cap 366. During use, the fluids that are in the chamber 304 may flow through the wicking material 315 to the reservoir 322. The reservoir 322 may store at least some of the fluids therein and/or position the fluids for removal by the conduit 108. In some examples, at least a portion of the wicking material 315 may extend continuously between at least a portion of the opening of the interior channel and chamber 304 to wick any fluid from the opening directly to the reservoir 322.

In some examples (not shown), the fluid impermeable coating 302 may be disposed on the cap 366, such as enclosing the cap 366 within the chamber 304.

In some examples, the sheath 352 may include at least a portion of the conduit 108 therein, such as at least partially disposed in the chamber 304. For example, the conduit 108 may extend from the sheath 352 to a region at least proximate to the opening 356. The region proximate to the opening 356 may be disposed near or on the skin around the male urethra (e.g., on the penis). Accordingly, when a patient lays on their back, fluid (e.g., urine) may aggregate near the opening 306 against the skin of the wearer. The fluid may be removed from the chamber 304 via the conduit 108. The conduit 108 may be disposed within the wicking material and includes the inlet positioned within the fluid collection device and an outlet configured to be fluidly coupled to a vacuum source.

The receptacle 350, the sheath 352, the cap 366, and the conduit 108 may be attached together using any suitable method. For example, at least two of the receptacle 350, the sheath 352, the cap 366, or the conduit 108 may be attached together using at least one of an interference fit, an adhesive, stitching, welding (e.g., ultrasonic welding), tape, any other suitable method, or combinations thereof.

In some examples, the vacuum source (not shown) may be remotely located from the sheath 352. In such examples, the conduit 108 may extend out of and away from the sheath 352 to the vacuum source or a fluid storage container. For example, the inlet of the conduit may be used to remove fluid from the chamber 304 via vacuum when an outlet (not shown) of the conduit 108 is fluidly coupled to the vacuum source or fluid storage container operably coupled to the vacuum source.

In some examples (not shown), the fluid collection device 300 does not include the cap 366. In such examples, the fluid impermeable coating 302 may include at least one aperture sized and shaped to receive and seal against the conduit 108, such as within the chamber 304. In such examples, the outlet of the conduit 108 may be fluidly coupled to a fluid storage container or vacuum device (not shown). Accordingly, the interior region of the chamber 304 may be fluidly coupled to the vacuum source via the conduit 108. As the vacuum source applies a vacuum/suction, the fluid in the chamber 304 may be removed through the conduit 108. In some examples, the fluid may be pumped through the vacuum source (not shown) into a section of the conduit 108 fluidly coupled to a fluid storage container (not shown) into which the fluid may be deposited.

In examples, portions of the chamber 304 may be substantially empty due to the varying sizes and rigidity of the male penis. However, in some examples (not shown), the outermost regions of the chamber 304 (e.g., periphery of the interior regions of the sheath 352) may include wicking material 315 in a position to blunt a stream of urine from the male urethra thereby limiting splashing and/or to direct the fluids to a selected region of the chamber 304. Since the chamber 304 is substantially empty (e.g., substantially all of the chamber 304 forms a reservoir), the fluids are likely to pool at a gravimetrically low point of the chamber 304. Depending on the orientation of the wearer, the gravimetrically low point of the chamber 304 may be at an intersection of the device and the skin of the wearer (proximate to opening 356), a corner formed in the sheath 352, the distal end region 34 of the chamber 304, or another suitable location. The inlet of the conduit 108 may be positioned to be in or proximate to the gravimetrically low point of the chamber 304 depending on the orientation of the user, such as when a user is on their back, side, or standing.

During operation, a male using the fluid collection device 300 may discharge fluids (e.g., urine) into the chamber 304. The fluids may pool or otherwise be collected in the chamber 304, such as against the skin of the user (e.g., wearer). At least some of the fluids may enter the interior of the conduit 108 via the inlet of the conduit. The fluid may be drawn out of the fluid collection device 300 via the vacuum/suction provided by the vacuum source. In some examples, during operation, the aperture 362 may substantially maintain the pressure in the chamber 304 at atmospheric pressure even though fluid is introduced into and subsequently removed from the chamber 304.

As the vacuum source (FIG. 4) applies a vacuum/suction in the conduit 108, the fluid(s) in the chamber 104 or 304 (e.g., at the second end region 244 such as in the reservoir 322) may be drawn into the inlet and out of the fluid collection device 100, 200, or 300 via the conduit 108.

Figure 4:
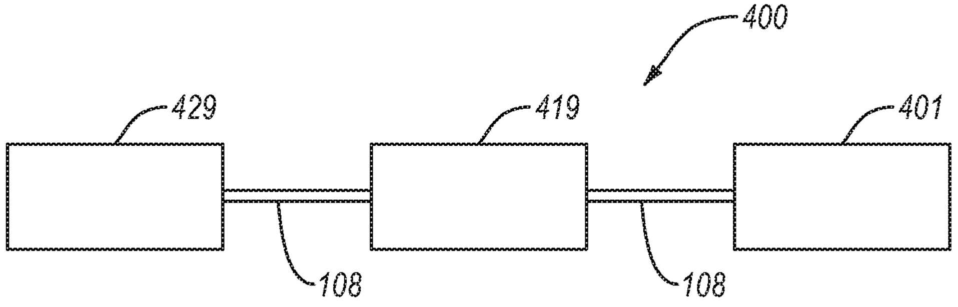
FIG. 4 is a block diagram of a system for fluid collection, according to an embodiment.

FIG. 4 is a block diagram of a system 400 for fluid collection, according to an embodiment. The system 400 includes a fluid collection device 401, a fluid storage container 419, and a vacuum source 429. The fluid collection device 401, the fluid storage container 419, and the vacuum source 429 may be fluidly coupled to each other via one or more conduits 108. For example, fluid collection device 401 may be operably coupled to one or more of the fluid storage container 419 or the (portable) vacuum source 429 via the conduits 108. The fluid collection device 401 may be similar or identical to any of the fluid collection devices disclosed herein, such as a male or female fluid collection device.

Fluid (e.g., urine or other bodily fluids) collected in the fluid collection device 401 may be removed from the fluid collection device 401 via the conduit 108 which protrudes into an interior region (e.g., chamber) of the fluid collection device 401. For example, a first open end of the conduit 108 may extend into the fluid collection device 401 to a reservoir therein. The second open end of the conduit 108 may extend into the fluid collection device 401 or the vacuum source 429. The suction force may be introduced into the interior region of the fluid collection device 401 via the first open end of the conduit 108 responsive to a suction (e.g., vacuum) force applied at the second end of the conduit 108. The suction force may be applied to the second open end of the conduit 108 by the vacuum source 429 either directly or indirectly.

The suction force may be applied indirectly via the fluid storage container 419. For example, the second open end of the conduit 108 may be fluid coupled to or disposed within the fluid storage container 419 and an additional conduit 108 may extend from the fluid storage container 419 to the vacuum source 429. Accordingly, the vacuum source 429 may apply suction to the fluid collection device 401 via the fluid storage container 419. As the fluid is drained from the chamber, the fluid may travel through the first section of conduit to the fluid storage container where it may be retained. Accordingly, fluid, such as urine, may be drained from the fluid collection device 401 using the vacuum source 429. In some examples, the suction force may be applied directly via the vacuum source 429. For example, the second open end of the conduit 108 may be disposed within the vacuum source 429. An additional conduit 108 may extend from the vacuum source 429 to a point outside of the fluid collection device 401, such as to the fluid storage container 419. In such examples, the vacuum source 429 may be disposed between the fluid collection device 401 and the fluid storage container 419.

In examples, the fluid storage container 419 may include a bag (e.g., drainage bag), a bottle or cup (e.g., collection jar), or any other enclosed container for storing bodily fluids such as urine.

The vacuum source 429 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 429 may provide a vacuum or suction to remove fluid from the fluid collection device 401. In examples, the vacuum source 429 may be powered by one or more of a power cord (e.g., connected to a power socket), one or more batteries, or even manual power (e.g., a hand operated vacuum pump). The vacuum sources 429 disclosed herein may include one or more of a switch, a button, a plug, a remote, or any other device suitable to activate the vacuum source 429.

Figure 5:
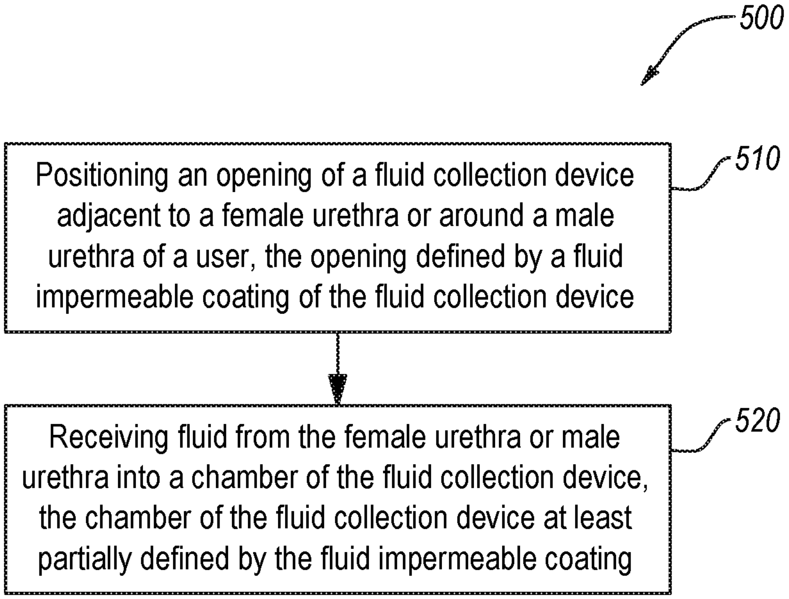
FIG. 5 is a flow diagram of a method to collect fluid, according to an embodiment.

FIG. 5 is a flow diagram of a method 500 to collect fluid, according to an embodiment. The method 500 may include act 510, which recites "positioning an opening of a fluid collection device adjacent to a female urethra or around a male urethra of a user, the opening defined by a fluid impermeable coating of the fluid collection device." Act 510 may be followed by act 520, which recites "receiving fluid from the female urethra or male urethra into a chamber of the fluid collection device, the chamber of the fluid collection device at least partially defined by the fluid impermeable coating."

Acts 510 and 520 of the method 500 are for illustrative purposes. For example, the act 510 and 520 of the method 500 may be performed in different orders, split into multiple acts, modified, supplemented, or combined. In an example, one or more of the acts 510 and 520 may be omitted from the method 500. For example, the method 500 may not include the act 510. Any of the acts 510 or 520 may include using any of the fluid collection devices, vacuum sources, fluid storage containers, systems, or components of the same disclosed herein. For example, the fluid collection device may include a fluid impermeable coating at least partially defining the chamber, the fluid impermeable coating also defining an opening extending therethrough, the opening configured to be positioned adjacent to a female urethra or have a male urethra positioned therethrough. The fluid collection device may include wicking material disposed with the chamber and a conduit disposed within the wicking material, the conduit including an inlet positioned within the fluid collection device and an outlet.

Act 510 recites "positioning an opening of a fluid collection device adjacent to a female urethra or around a male urethra of a user, the opening defined by a fluid impermeable coating of the fluid collection device." The fluid collection device may be a female fluid collection device, such as any of those disclosed herein. The fluid collection device may be a male fluid collection device, such as any of those disclosed herein. Positioning an opening of a fluid collection device adjacent to a female urethra of a user may include disposing the opening against, between, or inside the labia majora of the female user. Positioning an opening of a fluid collection device adjacent to a female urethra of a user may include disposing the second end region of the fluid collection device in the gluteal cleft of the female user. Positioning an opening of a fluid collection device adjacent to a female urethra or around a male urethra of a user may include securing the fluid collection device in position on the user, such as via tape, an adhesive, a wrap, inserting into clothing, etc. Positioning an opening of a fluid collection device around a male urethra of a user may include positioning the opening of the male fluid collection device around the penis of the user (e.g., wearer). In such an example, the method 500 may include positioning a sheath of the male fluid collection device in a hollowed region of the receptacle such that the male urethra is positioned through an opening of the sheath of the male fluid collection device.

Act 520 recites "receiving fluid from the female urethra or male urethra into a chamber of the fluid collection device, the chamber of the fluid collection device at least partially defined by the fluid impermeable coating." For example, act 520 may include wicking the fluids away from the urethra, such as using wicking material (e.g., fluid permeable membrane and a fluid permeable support) via the opening or chamber. The act 520 may include wicking the fluids away from the urethra such as to a reservoir in the fluid collection device. The act 520 may include flowing the fluid towards a portion of the chamber that is fluidly coupled to an inlet of a conduit for removing the fluid from chamber (e.g., conduit in fluid communication a vacuum source). For instance, act 520 may include flowing the fluids to a substantially unoccupied portion of the chamber (e.g., a reservoir), to a gravimetrically low point of the chamber, etc.

The method 500 may include applying suction with a vacuum source effective to suction the fluids from the chamber via a conduit disposed therein and fluidly connected to the vacuum source. In examples, applying suction with a vacuum source effective to suction the fluids from the chamber via a conduit disposed therein and fluidly coupled to the vacuum source may include using any of the vacuum sources disclosed herein. In an example, applying suction may include activating the vacuum source (e.g., suction device) in fluid communication with the inlet of the conduit in the fluid collection device. In examples, activating the vacuum source in fluid communication with the inlet of the conduit in the fluid collection device may include supplying power to the vacuum source by one or more of flipping an on/off switch, pressing a button, plugging the vacuum source into a power outlet, putting batteries into the vacuum source, etc. In examples, the vacuum source may include a hand operated vacuum pump and applying suction with a vacuum source may include manually operating the hand operated vacuum pump effective to suction the fluids from the chamber.

In examples, applying suction with a vacuum source effective to suction the fluids from the chamber may be effective to remove at least some fluid (e.g., urine) from the chamber of the fluid collection device. In examples, applying suction with a vacuum source effective to suction the fluids from the chamber via a conduit disposed therein and fluidly coupled to the vacuum source may be effective to transfer at least some of the fluid from the chamber of the fluid collection device to a fluid storage container (e.g., a bottle or bag) fluidly coupled thereto. In examples, the vacuum source may be spaced from the fluid collection device.

In examples, applying suction with a vacuum source effective to suction the fluids from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller, or may merely provide an indication that a level of moisture is present that may necessitate removal of fluid from the chamber of the fluid collection device. In the latter case, a user may receive the indication and activate the vacuum pump.

In an example, the method 500 may include collecting the fluids that are removed from the fluid collection device, such as into a fluid storage container that is spaced from the fluid collection device and fluidly coupled to the conduit. The fluid storage container may include any of the fluid storage containers disclosed herein.

Figure 6:
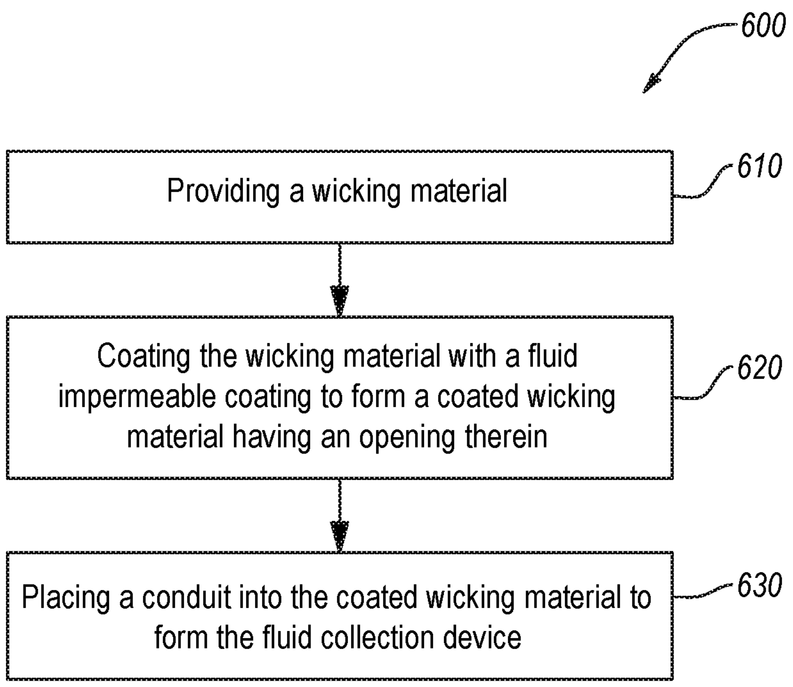
FIG. 6 is a flow diagram of a method to making a fluid collection device, according to an embodiment.

FIG. 6 is a flow diagram of a method 600 to making a fluid collection device, according to an embodiment. The method 600 may include act 610, which recites "providing a wicking material." Act 610 may be followed by act 620, which recites "coating the wicking material with a fluid impermeable coating to form a coated wicking material having an opening therein." Act 620 may be followed by act 630, which recites "placing a conduit into the coated wicking material to form the fluid collection device."

Acts 610, 620, and 630 of the method 600 are for illustrative purposes. For example, the act 610, 620, and 630 of the method 600 may be performed in different orders, split into multiple acts, modified, supplemented, or combined. In an example, one or more of the acts 610, 620, and 630 of the method 600 may be omitted from the method 600. For example, the method 600 may not include the act 630. Any of the acts 610, 620, or 630 may include using any of the fluid collection devices, vacuum sources, fluid storage containers, systems, or components of the same disclosed herein. For example, the fluid impermeable coating at least partially defines the chamber, an opening extending therethrough, where the opening is sized and shaped to be positioned adjacent to a female urethra or have a male urethra positioned therethrough. The fluid collection device formed by the method 600 may include any of the fluid collection devices disclosed herein. For example, the fluid collection device may include wicking material disposed with the chamber and a conduit disposed within the wicking material, the conduit including an inlet positioned within the fluid collection device and an outlet.

Act 610 recites "providing a wicking material." Providing a wicking material may include providing any of the wicking materials in any of the configurations disclosed herein. For example, providing the wicking material may include providing a cylindrically shaped wicking material, such one or more of a cylindrically shaped fluid permeable membrane or a fluid permeable support. Providing the wicking material may include providing the wicking material of any of the female fluid collection devices disclosed herein. For example, the fluid permeable support may be concentrically disposed in the fluid permeable membrane. The fluid permeable support may include a channel formed therethrough to accommodate the conduit.

Providing the wicking material may include providing the wicking material of any of the male fluid collection devices disclosed herein. For example, providing the wicking material may include providing the fluid permeable membrane concentrically disposed within the fluid permeable support. The fluid permeable support and fluid permeable membrane may have a channel formed therein to allow a conduit to be inserted therein.

Act 620 recites "coating the wicking material with a fluid impermeable coating to form a coated wicking material having an opening therein." Coating the wicking material with a fluid impermeable coating to form a coated wicking material having an opening therein includes applying the coating onto the wicking material effective to coat or impregnate the outer surface of the wicking material with the fluid impermeable coating material to form the opening in the fluid impermeable coating. The opening may be as described herein for the female fluid collection device or the male fluid collection device.

Coating the wicking material with a fluid impermeable coating to form a coated wicking material having an opening therein may include utilizing any of the fluid impermeable coating materials disclosed herein in any of the thicknesses, surface characteristics, or shapes disclosed herein. Coating the wicking material with a fluid impermeable coating to form a coated wicking material having an opening therein may include one or more of dipping (e.g., dip coating), spraying (e.g., spray coating), wrapping (e.g., shrink wrapping), brush application, rolling, casting, impregnation (e.g., vacuum infiltration), or the like. For example, the opening may be formed by masking a portion of the wicking material with a masking agent and dip coating the wicking material (and optionally, the first and second endcaps) in the fluid impermeable coating material. After the fluid impermeable coating material dries, the masking agent may be removed from the wicking material to reveal the opening. In some examples, coating the wicking material with a fluid impermeable coating to form a coated wicking material having an opening therein may include coating only the portions of the wicking material (or endcaps) with the fluid impermeable coating material outside of a selected dimension and location of selected opening. Accordingly, selective application of the fluid impermeable coating material may be used to form the opening.

Act 630 recites "placing a conduit into the coated wicking material to form the fluid collection device." Placing a conduit into the coated wicking material to form the fluid collection device may include inserting the conduit into the coated wicking material to a distance therein. For example, the conduit may be inserted into and through the wicking material to a reservoir in the chamber of the fluid collection device. In some examples, placing a conduit into the coated wicking material may include disposing the conduit into the wicking material to a point within the wicking material or until the inlet of the conduit is co-extensive with the wicking material. Placing a conduit into the coated wicking material may include inserting the conduit through the coating.

Placing a conduit into the coated wicking material to form the fluid collection device may include disposing a conduit within the coated wicking material sufficient to form any of the fluid collection devices disclosed herein, such as a female fluid collection device or male fluid collection device.

In some examples, prior to coating, the method 600 may include disposing an endcap on one or more ends of the wicking material, such as placing any of the endcaps or caps on any of the ends of the coated wicking materials disclosed herein. For example, the method 600 may include placing an endcap on each end of a fluid permeable membrane disposed on a cylindrical fluid permeable support. Placing the endcap on the second end of a coated wicking material may form a reservoir in the chamber, such as between the endcap and the wicking materials. In such examples, the coating may be disposed over or under the endcaps or caps. In some examples, disposing an endcap on one or more ends of the wicking material may be carried out after coating at least a portion of the wicking material with the coating. In some examples, disposing the endcap on one or more ends of the wicking material may include adhering the endcaps to one or more of the wicking material or the fluid impermeable coating.

In some examples, the method 600 may include connecting, indirectly or directly, the conduit of the fluid collection device to a vacuum source. For example, connecting the conduit of the fluid collection device to a vacuum source may include connecting the conduit to the fluid storage container. Connecting the conduit of the fluid collection device to a vacuum source may include forming any of the systems disclosed herein.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A fluid collection device, comprising:

at least one wicking material including an outer surface;

a fluid impermeable coating at least partially embedded within the at least one wicking material at the outer surface, the fluid impermeable coating defining a chamber within the fluid collection device partially enclosing the at least one wicking material and defining an opening through which a portion of the at least one wicking material is exposed, the opening configured to be positioned adjacent to a female urethra or have a male urethra positioned therethrough; wherein the fluid impermeable coating defines an aperture configured to receive a conduit.

2. The fluid collection device of claim 1, wherein the at least one wicking material includes one or more of a fluid permeable membrane or a fluid permeable support.

3. The fluid collection device of claim 1, wherein an outermost portion of the fluid impermeable is coextensive within an outermost portion of the at least one wicking material.

4. The fluid collection device of claim 1, wherein the fluid impermeable coating includes one or more of a polymer, a wax, nanocellulose, or nanoparticles.

5. The fluid collection device of claim 1, wherein the fluid impermeable coating includes a superhydrophobic material.

6. The fluid collection device of claim 1, wherein the fluid collection device is configured as a female fluid collection device.

7. The fluid collection device of claim 1, wherein the fluid collection device is configured as a male fluid collection device.

8. The fluid collection device of claim 1, wherein the fluid collection device is substantially cylindrical.

9. The fluid collection device of claim 1, wherein the at least one wicking material is disposed in a substantially cylindrical configuration.

10. The fluid collection device of claim 9, further comprising a first endcap disposed over a first end of the cylindrical configuration and a second endcap disposed over a second end of the cylindrical configuration, wherein the first endcap and the second endcap retain the wicking material in the cylindrical configuration.

11. The fluid collection device of claim 10, wherein the fluid impermeable coating is disposed on a portion of the wicking material and the first endcap and the second endcap.

12. The fluid collection device of claim 1, further comprising the conduit disposed within the chamber, the conduit including an inlet positioned within the chamber and an outlet configured to be fluidly coupled to a vacuum source.

13. A fluid collection system, comprising:

a fluid storage container configured to hold a fluid;

a fluid collection device including:

at least one wicking material including an outer surface;

a fluid impermeable coating at least partially embedded within the at least one wicking material at the outer surface, the fluid impermeable coating defining a chamber within the fluid collection device and defining an opening through which a portion of the at least one wicking material is exposed, the opening configured to be positioned adjacent to a female urethra or have a male urethra positioned therethrough;

a conduit disposed within the chamber, the conduit including an inlet positioned within the chamber and an outlet configured to be fluidly coupled to a vacuum source; and a vacuum source fluidly coupled to one or more of the fluid storage container or the outlet of the fluid collection device, the vacuum source configured to draw fluid from the fluid collection device.

14. The fluid collection system of claim 13, wherein the at least one wicking material includes one or more of a fluid permeable membrane or a fluid permeable support.

15. The fluid collection system claim 14, wherein an outermost portion of the fluid impermeable coating is coextensive with an outermost portion of the fluid permeable membrane.

16. The fluid collection system of claim 13, wherein the fluid impermeable coating includes one or more of a polymer, a wax, nanocellulose, or nanoparticles.

17. The fluid collection system of claim 13, wherein the fluid impermeable coating includes a superhydrophobic material.

18. A method to collect fluid, the method comprising:

positioning an opening of a fluid collection device adjacent to a female urethra or around a male urethra of a user the fluid collection device including:

at least one wicking material including an outer surface; and a fluid impermeable coating at least partially embedded within the at least one wicking material at the outer surface, the fluid impermeable coating defining a chamber within the fluid collection device partially enclosing the at least one wicking material and defining the opening through which a portion of the at least one wicking material is exposed, the opening configured to be positioned adjacent to a female urethra or have a male urethra positioned therethrough; and receiving fluid from the female urethra or male urethra into the chamber of the fluid collection device.

19. The method of claim 18, further comprising applying suction with a vacuum source effective to suction the fluids from the chamber via a conduit disposed therein and fluidly coupled to the vacuum source.

20. The method of claim 19, wherein applying suction with a vacuum source effective to suction the fluid from the chamber via a conduit disposed therein and fluidly coupled to the vacuum source includes transferring at least some of the fluid from the chamber of the fluid collection device to a fluid storage container operably coupled thereto.

* * * * *